United States Patent
Holmes et al.

(10) Patent No.: US 11,141,814 B2
(45) Date of Patent: Oct. 12, 2021

(54) THERMOGRAPHIC INSPECTION FOR TAPE LAYUP MACHINES

(71) Applicant: The Boeing Company, Chicago, IL (US)

(72) Inventors: Tyler Holmes, Seattle, WA (US); Amanda Hansen, Seattle, WA (US); Steven K. Brady, Renton, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 16/292,004

(22) Filed: Mar. 4, 2019

(65) Prior Publication Data
US 2020/0282494 A1 Sep. 10, 2020

(51) Int. Cl.
| | | |
|---|---|---|
| *B32B 41/00* | (2006.01) | |
| *B23K 26/03* | (2006.01) | |
| *B29C 70/38* | (2006.01) | |
| *B29C 65/00* | (2006.01) | |

(52) U.S. Cl.
CPC .......... *B23K 26/034* (2013.01); *B23K 26/032* (2013.01); *B29C 66/301* (2013.01); *B29C 70/384* (2013.01); *B29C 70/386* (2013.01)

(58) Field of Classification Search
CPC .. B23K 26/034; B23K 26/032; B29C 66/301; B29C 70/384; B29C 70/386
USPC .......................... 156/64, 350, 351, 378, 379
See application file for complete search history.

(56) References Cited

U.S. PATENT DOCUMENTS

| | | |
|---|---|---|
| 7,495,758 B2 | 2/2009 | Walton |
| 7,555,404 B2 | 6/2009 | Brennan et al. |
| 8,753,458 B2 | 6/2014 | Engelbart et al. |
| 10,928,340 B2 | 2/2021 | Johnson et al. |
| 2006/0191622 A1 | 8/2006 | Ritter et al. |
| 2007/0029030 A1 | 2/2007 | McCowin |
| 2012/0330453 A1 | 12/2012 | Sangari et al. |
| 2014/0124120 A1 | 5/2014 | Pham et al. |
| 2015/0254835 A1 | 9/2015 | Dorris et al. |
| 2016/0102966 A1 | 4/2016 | Grossnickle et al. |
| 2016/0102973 A1 | 4/2016 | Gonze et al. |
| 2017/0320242 A1* | 11/2017 | Kok ...................... B29C 70/386 |
| 2017/0350764 A1 | 12/2017 | Thompson et al. |

FOREIGN PATENT DOCUMENTS

EP          1574845 A1     9/2005

OTHER PUBLICATIONS

Abdel-Fattah et al., "Behavior of air jet impinging on curved surfaces," Journal of Aerospace Engineering, vol. 27 Issue 5—Sep. 2014, 2 pages, Abstract only.
Automated Fiber Placement; Wikipedia; Feb. 18, 2019.
German Search Report; dated Jan. 10, 2019.

(Continued)

*Primary Examiner* — Michael N Orlando
*Assistant Examiner* — Joshel Rivera
(74) *Attorney, Agent, or Firm* — Duft & Bornsen, PC

(57) ABSTRACT

Systems and methods are provided for thermal inspection of tape layup. One embodiment is a method for performing inspection of a tape layup. The method comprises laying up tape onto a surface of a laminate, applying heat to tack the tape to the surface, and generating thermographic images of the tape as applied to the surface.

22 Claims, 16 Drawing Sheets

(56) References Cited

OTHER PUBLICATIONS

Kendoush et al, "Theory of stagnation region heat and mass transfer to fluid jets impinging normally on solid surfaces," Chemical Engineering and Processing: Process Intensification vol. 37, Issue 3, May 1998, pp. 223-228, 2 pages, Abstract Only.
NASA Langley Research Center; In Situ Thermographic Inspection.
New et al., "Dynamics of laminar circular jet impingement upon convex cylinders," Physics of Fluids, vol. 27, Issue 2, 10.1063/1.4913498, Feb. 2015, 8 pages, Abstract only.
Peter D Juarez et al; In Situ Thermal Inspection of Automated Fiber Placement Operations for Tow and Ply Defect Detection; NASA Langley Research Center.
Rau et al., "Enhanced Two-Phase Impingement Technologies for Electronics Cooling," School of Mechanical Engineering, Purdue University, Apr. 14, 2016, 13 pages.
Andrea Lanfermann et al; Quality monitoring of laser-beam-welded tapes made of fibre-reinforced plastics by means of thermography. XP-002796285; Joining Plastics 2018.
Nederland Search Report; Application NL2022882; dated Dec. 12, 2019
Nederland Search Report; Application NL2022885; dated Dec. 16, 2019.
Nederland Search Report; Application NL2022886; dated Dec. 16, 2019.
Nederland Search Report; Application NL2022887; dated Jan. 2, 2020.
European Search Report; Application EP20160703; dated Jul. 20, 2020.
European Search Report; Application EP20160705; dated Jul. 17, 2020.
European Search Report; Application EP20160731; dated Jul. 20, 2020.
European Search Report; Application EP20160754; dated Jul. 20, 2020.

\* cited by examiner

TAPE LANE ANALYSIS (THERMOSET)

TAPE LANE ANALYSIS (THERMOSET)

TAPE LANE ANALYSIS (THERMOPLASTIC)

DEBRIS DETECTION

THERMOGRAPHIC INSPECTION FOR TAPE LAYUP MACHINES

FIELD

The disclosure relates to the field of fabrication, and in particular, to tape layup machines that create laminates comprising multiple layers of tape.

BACKGROUND

Multi-layer laminates of constituent material (e.g., Carbon Fiber Reinforced Polymer (CFRP)) may be formed into any of a variety of shapes for curing into a composite part. To facilitate the fabrication of composite parts, a tape layup machine, such as an Automated Fiber Placement (AFP) machine or Automated Tape Layup (ATL) machine, may be utilized. For example, a tape layup machine may lay up one or more layers of tows of constituent material that form a laminate which is then hardened (e.g., cured or consolidated) to form a composite part.

The operations of a tape layup machine may be directed by a Numerical Control (NC) program that dictates movements of the tape layup machine. A tape layup machine may dispense multiple tows at once onto a laminate in a single course (e.g., a single "run" across a laminate), and a tape layup machine may initiate or terminate individual lanes of tape within a course at different locations, in response to instructions from the NC program.

The final laminate generated by a tape layup machine may vary from what is intended in an NC program, owing to factors that are not always controllable. For example, lanes of tape may be placed some distance apart from their intended locations due to the machine being in need of calibration, foreign debris may fall onto the laminate, and fabrication inconsistencies such as twists or folds within a lane of tape may occur owing to inconsistencies in the lamination process. These conditions are difficult to visually detect during layup, because lanes of tape are made of the same material and hence are the same color (e.g., black). Furthermore, human inspection of a laminate prior to curing may result in additional foreign debris (e.g., lint, etc.) landing upon the laminate. Furthermore, current inspection techniques do not allow real time course by course inspection of the lay down process. The above-recited problems also apply to laminates made from tapes that are not fiber reinforced, and laminates that are not capable of hardening into composite parts. It is desirable to detect all conditions described above, and especially desirable to detect conditions cause portions of layup to be out of tolerance.

It remains possible to perform inspection of a composite part via ultrasonic techniques after hardening a laminate. However, if out of tolerance conditions within the composite part indicate a level of quality below a desired level, the entire composite part may need to be reworked or discarded. For large composite parts such as aircraft wings, a single reworked or discarded composite part results in a substantial waste of resources, time, and labor.

Therefore, it would be desirable to have a method and apparatus that take into account at least some of the issues discussed above, as well as other possible issues.

SUMMARY

Embodiments described herein include thermographic inspection systems that are mounted to the head of a tape layup machine. These inspection systems utilize infrared cameras to acquire thermal images of lanes of tape applied by the head. Different portions of the laminate will exhibit different temperatures, depending on whether they are the underlying laminate, foreign debris, or lanes of tape applied atop the underlying laminate. For example, a heater at the head may generate a detectable temperature difference between the underlying laminate and the lanes of tape, by heating either the underlying laminate or the lanes of tape. In a further example, a heater may heat both a laminate and a foreign object on the laminate. However, because the laminate and the foreign object have fundamentally different thermal properties, the foreign object will respond to the application of heat differently than the underlying laminate, resulting in a detectable difference in temperature. These differences are detected by reviewing thermal images acquired during the layup process. The location and nature of features that impact the quality of the laminate may therefore be reliably detected and reported, by analyzing thermal images from infrared cameras mounted to a head of the tape layup machine. One embodiment is a method for performing inspection of a tape layup. The method comprises laying up tape onto a surface of a laminate, applying heat to tack the tape to the surface, and generating thermographic images of the tape as applied to the surface.

A further embodiment is a method for determining applied tape boundaries. The method includes laying up lanes of tape onto a surface of a laminate, applying heat to tack the lanes of tape to the surface of the laminate, generating thermographic images of the lanes of tape as applied to the laminate, analyzing contrast within the thermographic images to identify the lanes of tape, and reporting locations of ends of the lanes of tape, based on boundaries depicted in the thermographic images.

A further embodiment is a non-transitory computer readable medium embodying programmed instructions which, when executed by a processor, are operable for performing a method for performing tape layup inspection. The method includes laying up lanes of tape onto a surface of a laminate, applying heat to tack the lanes of tape to the surface of the laminate, generating thermographic images of the lanes of tape as applied to the laminate, analyzing contrast within the thermographic images to identify the lanes of tape, and reporting locations of ends of the lanes of tape, based on boundaries depicted in the thermographic images.

A still further embodiment is a tape layup end detection system. The system includes a head of a tape layup machine. The head includes tape dispensers that lay up lanes of tape onto a surface of a laminate, a heater that applies heat to tack the lanes of tape to the surface, and an infrared camera disposed downstream of the tape dispensers that generates thermographic images of the lanes of tape as applied to the laminate. The system also includes a controller that analyzes contrast within the thermographic images to identify the lanes of tape, and reports locations of ends of the lanes of tape, based on boundaries depicted in the thermographic images.

A still further embodiment is a method of controlling a tape laying process. The method comprises laying up tape on surface, while laying up the tape, inspecting the surface on which it is laid up as well as the laid-up tape using IR imaging, reviewing the IR imaging for out of tolerance conditions, and stopping the tape laying if an out of tolerance condition is detected.

A still further embodiment is a method of detecting out of tolerance inconsistencies during a tape laying process. The method comprises heating a surface on which a tape will be applied, acquiring an IR image of the surface, and determining that an out of tolerance inconsistency is depicted in the IR image.

A still further embodiment is a method of inspecting a composite surface. The method includes creating temperature differentials on a surface that has been heated, detecting the temperature differentials on the surface, and determining that an out of tolerance inconsistency is present based upon the temperature differentials.

A still further embodiment is a method of creating a composite structure. The method includes inspecting a surface on which a laminate is to be laid, with IR imaging, reviewing the IR imaging for out of tolerance conditions, and stopping tape layup prior to reaching an out of tolerance condition.

A still further embodiment is a method that includes laying up lanes of tape at a laminate, operating an IR camera to thermally image the lanes of tape, reviewing thermal images to identify ends of the lanes of tape, and determining whether an end of a lane of tape is out of tolerance, and reporting the out of tolerance lane of tape for dispositioning.

Other illustrative embodiments (e.g., methods and computer-readable media relating to the foregoing embodiments) may be described below. The features, functions, and advantages that have been discussed can be achieved independently in various embodiments or may be combined in yet other embodiments further details of which can be seen with reference to the following description and drawings.

DESCRIPTION OF THE DRAWINGS

Some embodiments of the present disclosure are now described, by way of example only, and with reference to the accompanying drawings. The same reference number represents the same element or the same type of element on all drawings.

DESCRIPTION

The figures and the following description provide specific illustrative embodiments of the disclosure. It will thus be appreciated that those skilled in the art will be able to devise various arrangements that, although not explicitly described or shown herein, embody the principles of the disclosure and are included within the scope of the disclosure. Furthermore, any examples described herein are intended to aid in understanding the principles of the disclosure, and are to be construed as being without limitation to such specifically recited examples and conditions. As a result, the disclosure is not limited to the specific embodiments or examples described below, but by the claims and their equivalents.

As used herein, "tape" may comprise fiber reinforced tapes or slit tape tows. In this disclosure the terms tape and tow are used interchangeably to indicate strips of material of varying widths. Tapes may be utilized to fabricate a variety of laminates, including laminates that will be cured into composite parts. Composite parts, such as Carbon Fiber Reinforced Polymer (CFRP) parts, are initially laid-up in a multi-layer laminate. Individual fibers within each layer of the laminate are aligned parallel with each other within the plane of the laminate, but different layers may exhibit different fiber orientations in order to increase the strength of the resulting composite along different dimensions. The laminate may include a viscous resin that solidifies in order to harden the preform into a composite part (e.g., for use in an aircraft). Carbon fiber that has been impregnated with an uncured thermoset resin or a thermoplastic resin is referred to as "prepreg." Other types of carbon fiber include "dry fiber" which has not been impregnated with thermoset resin but may include a tackifier or binder. Dry fiber may be infused with resin prior to curing. For thermoset resins, the hardening is a one-way process referred to as curing. For thermoplastic resins, a hardened (or consolidated) resin may reach a viscous form if it is re-heated.

Figure 1:
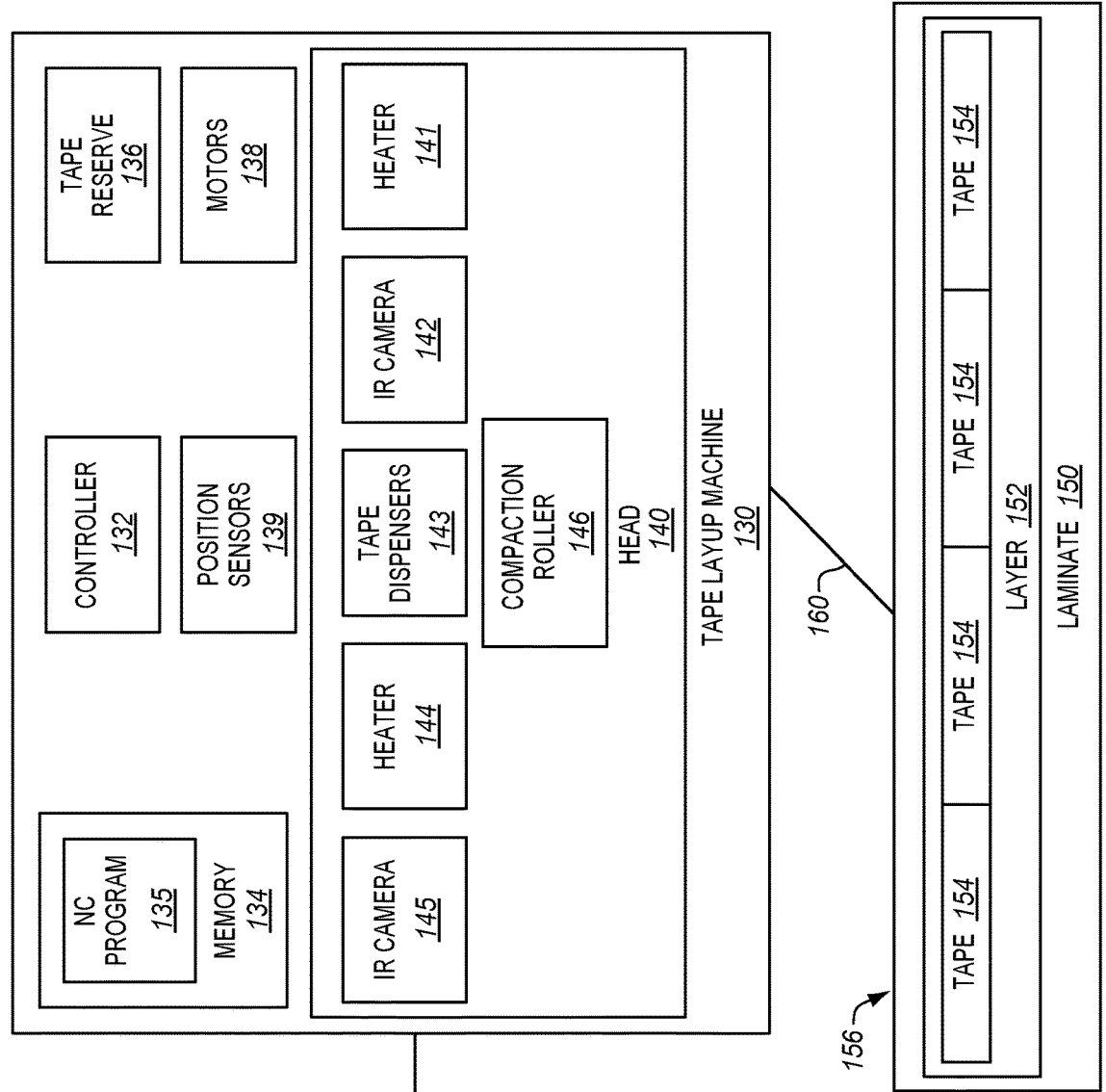
FIG. 1 is a block diagram of a tape layup inspection system in an illustrative embodiment.

FIG. 1 is a block diagram of a tape layup inspection system 100 in an illustrative embodiment. Tape layup inspection system 100 comprises any system, component, or device operable to lay up tape to form a laminate, and to inspect the laminate for quality control purposes. Tape layup inspection system 100 has been enhanced to utilize thermal imaging devices mounted to a head of a tape layup machine in order to identify features that may be pertinent to quality control.

In this embodiment, tape layup inspection system 100 includes inspection server 110 and tape layup machine 130. Tape layup machine 130 operates head 140 in accordance with NC program 135 in order to lay up lanes 160 of tape 154 that form one or more layers 152 of laminate 150. For example, controller 132 of tape layup machine 130 may direct the operations of motors 138 based on instructions stored in memory 134, in order to move head 140 to various locations at laminate 150. Controller 132 may further direct tape reserve 136 to provide additional tape to tape dispensers 143 of head 140. Controller 132 may be implemented, for example, as custom circuitry, as a hardware processor executing programmed instructions, or some combination thereof.

Head 140 includes tape dispensers 143, which apply lanes 160 of tape 154 to surface 156 of laminate 150. Heater 141 and/or heater 144 apply heat that facilitates tacking of lanes of tape 154 to laminate 150. For example, these heaters may heat laminate 150 (or lanes 160 of tape 154) to a temperature at which a thermoplastic or thermoset resin within the lanes of tape 154 either tackifies or becomes molten. Heaters 141 and 144 may comprise lasers, infrared heat lamps, etc.

In embodiments where heaters 141 and 144 heat either laminate 150 or the lanes of tape, a substantial temperature difference (e.g., one to fifty degrees Fahrenheit (F) for thermoset tapes, five hundred to eight hundred degrees Fahrenheit for thermoplastic tapes) exists between the lanes 160 of tape 154 and the laminate 150. This means that thermographic images (having a sensitivity of, for example, a fifth of one degree Fahrenheit) will exhibit a high degree of contrast between the lanes 160 of freshly laid tape and the laminate 150.

In embodiments where heaters 141 and 144 are operated to heat the lanes 160 of tape 154 and also the laminate 150, foreign objects (which are made from different types of material) will contrast strongly against the underlying laminate material, because they will reach a different temperature and have a different thermal emissivity than the laminate material in response to being exposed to the same amount of heat.

Head 140 also includes a compaction roller 146, which applies pressure to the lanes 160 of tape 154 (e.g., after the lanes 160 have been tackified), pressing them onto laminate 150 and physically integrating them into laminate 150. Infrared (IR) cameras 142 and 145 image the laminate 150 as well as the lanes 160 of tape 154 that are applied to laminate 150. Position sensors 139 detect the location of head 140 as thermographic images are acquired by IR cameras 142 and 145. This enables pixels within the thermographic images to be correlated with real-world locations at the laminate 150. Position sensors 139 may, for example, comprise laser or visual tracking systems, rotation and/or extension sensors mounted to actuators within tape layup machine 130, etc.

Thermographic images 118 produced by tape layup machine 130 during layup are processed by inspection server 110. Inspection server 110 includes controller 112, which analyzes thermographic images 118 stored in memory 114, and identifies and classifies features within the thermographic images 118 based on detection functions 122. Detection functions 122 may also include instructions for implementing one or more of the methods described herein. Controller 112 further determines, based on position data 120 acquired from position sensors 139, locations of the features on the laminate 150. This information may be passed on to a technician either as a report or an annotated image of the laminate for review. Controller 112 may be implemented, for example, as custom circuitry, as a hardware processor executing programmed instructions, or some combination thereof.

Figure 2:
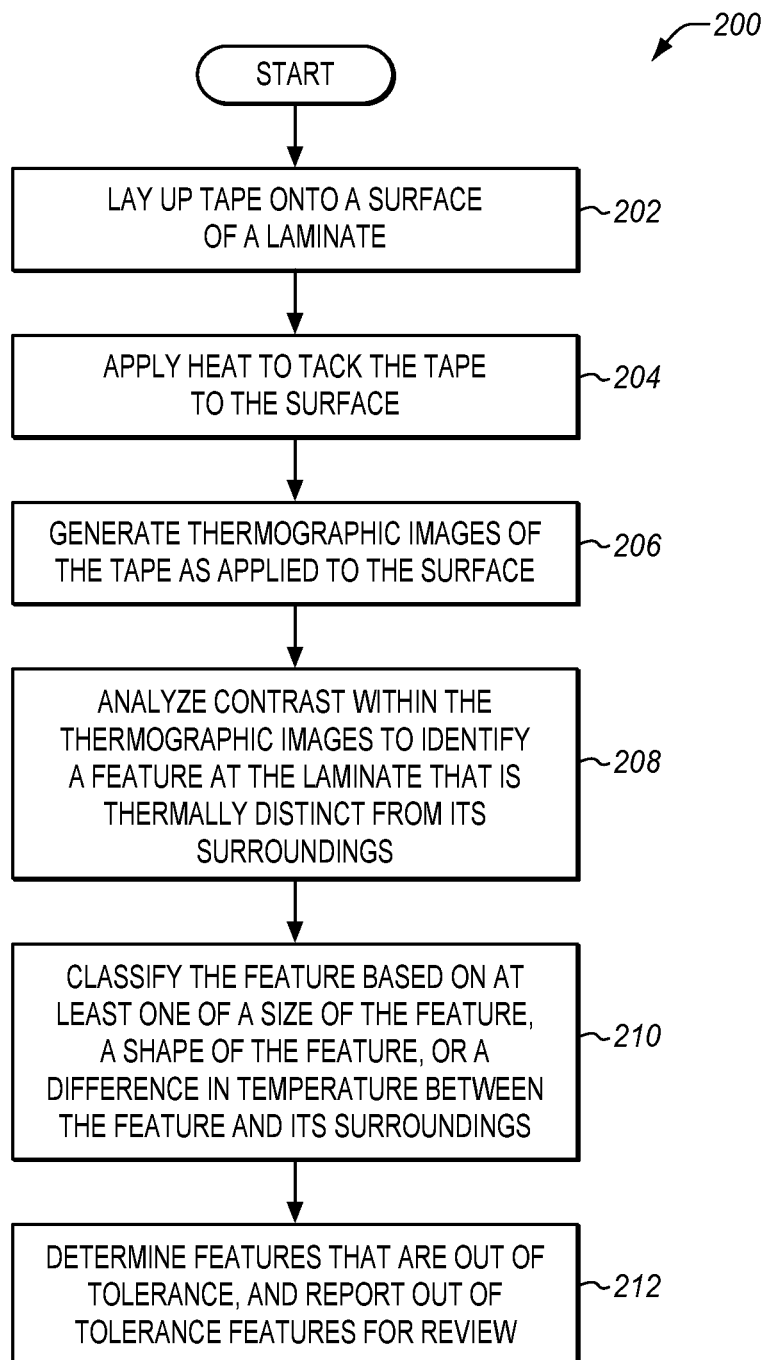
FIG. 2 is a flowchart illustrating a method for detecting and classifying features found within a layup for a laminate, based on thermographic images in an illustrative embodiment.

Illustrative details of the operation of tape layup inspection system 100 will be discussed with regard to FIG. 2. Specifically, FIG. 2 illustrates a method for detecting and classifying features found within a layup for a laminate, based on thermographic images. Assume, for this embodiment, that tape layup machine 130 has been programmed to follow instructions in NC program 135 for laying up a laminate (e.g., a laminate that will be hardened into a composite part). Further, assume that tape layup machine 130 is loaded with rows of tape (e.g., prepreg thermoset or thermoplastic CFRP) and is ready to initiate fabrication of the laminate. To this end, the tape layup machine 130 operates head 140 to lay up a base layer of the laminate 150 by dispensing one or more courses comprising lanes of tape.

FIG. 2 is a flowchart illustrating a method for operating a tape layup inspection system in an illustrative embodiment. The steps of method 200 are described with reference to tape layup inspection system 100 of FIG. 1, but those skilled in the art will appreciate that method 200 may be performed in other systems. The steps of the flowcharts described herein are not all inclusive and may include other steps not shown. The steps described herein may also be performed in an alternative order.

In step 202, head 140 of tape layup machine 130 lays up tape 154 onto surface 156 of laminate 150. This may comprise following instructions in NC program 135 to cut and/or dispense multiple lanes of tape in a course. This may further comprise operating compaction roller 146 to physically integrate the newly dispensed lanes of tape with the laminate 150.

In step 204, heater 141 or heater 144 apply heat to tack the lanes of tape to the surface of the laminate 150. Step 204 may occur concurrently with, before, or even after step 202. Thus, in many embodiments, laminate 150 or lanes 160 are heated prior to contacting each other. In embodiments where the tape 154 comprises a prepreg thermoset resin tape, heater 141 may be activated to alter the temperature of the surface of laminate 150 with respect to ambient temperature before the lanes of tape are applied to the surface. In embodiments where the tape 154 comprises prepreg thermoplastic tape, heater 144 may comprise one or more lasers that heat the tape 154 resulting in a temperature differential from approximately four hundred to eight hundred degrees Fahrenheit between the surface of the laminate before the tape 154 is applied. In either case, the heaters generate a substantial difference in temperature, between the lanes of the tape 154 leaving the tape dispenser 143, and the surface of laminate 150.

In step 206, IR camera 145 generates thermographic images 118 of the lanes 160 of the tape 154 as applied to the laminate 150. Each thermographic image 118 may depict a portion of all lanes within a course, and thermographic images 118 may be stitched together to depict the layup resulting from an entire course. Because lanes may extend for tens of feet, multiple thermographic images 118 may need to be analyzed in order to detect the specific start locations and stop locations of individual lanes within a course. Thus, the thermographic images 118 may be acquired periodically (e.g., once every few seconds, once every ten feet of movement of head 140, etc.), to ensure that there are no gaps in coverage between images during layup.

In step 208, controller 112 analyzes contrast within the thermographic images 118 to identify a feature at laminate 150 that is thermally distinct from its surroundings. Each pixel within a thermographic image 118 is assigned a value corresponding with a temperature, and thermally distinct features may be detected by identifying contiguous sets of pixels that are within a range of temperatures (e.g., fifty degrees Fahrenheit, ten degrees Fahrenheit, etc.) that are surrounded by pixels outside of the range (e.g., more than one degree Fahrenheit different than the contiguous set of pixels). Each feature may have an associated temperature or range of temperatures, a known shape, and a known size in terms of width or number of pixels. In further embodiments, a thermographic image may be altered by applying an edge detection algorithm (such as a Laplacian or other filter) before the image is analyzed.

In step 210, controller 112 classifies the feature based on at least one of a size of the feature, a shape of the feature, or a difference in temperature between the feature and its surroundings. For example, lanes 160 of tape 154 are expected to exhibit known ranges of temperature differences from an underlying laminate. These ranges are discussed above. If a region is within the expected range of temperature difference with respect to another region, it may be classified based on whether is hotter or colder than that other region.

In step 212 controller 112 determines features that are out of tolerance (e.g., too large, as identified by a filtering process performed on the feature's properties). If features are out of tolerance, then controller 112 reports the out of tolerance features for review. These features/conditions may be reported graphically on a representation of laminate 150, or in a textual report. During this step, controller 112 may further filter the features based on their size and type, in order to automatically indicate and highlight out of tolerance features without a need for human intervention.

In a further example, a feature that exhibits rounded borders (e.g., a puddle of liquid) may be classified differently than a feature having sharp, linear edges (e.g., an edge of a lane of tape). Size also plays a role in these determinations, as small features may be indicative of debris at the laminate, while large features may be indicative of entire courses or lanes of tape.

Method 200 provides a substantial advantage over prior inspection techniques, because it utilizes differences in temperature, not color, to identify and classify layup features. For example, there is likely to be a pre-existing temperature difference between layup components (e.g., because one of them is heated to facilitate tacking), while there is likely to be almost no color difference between the laminate and the lanes of tape in visible light spectra. Therefore, method 200 enables the signal to noise ratio of layup inspection techniques to increase by orders of magnitude with respect to prior techniques. Furthermore, because thermal imaging technology is tightly coupled with the head 140 of the tape layup machine 130, there is no need for manual imaging of the laminate, or other human interactions with the laminate 150. This reduces the chance of technicians dropping foreign debris onto the laminate, stepping on the laminate 150, or otherwise unintentionally altering the laminate 150 during human inspection. This also enables layup inspection to be performed much faster, and to occur contemporaneously with tape laydown of each course for each layer of the laminate, especially compared with stopping tape lay down to facilitate human access/inspection.

Figure 3:
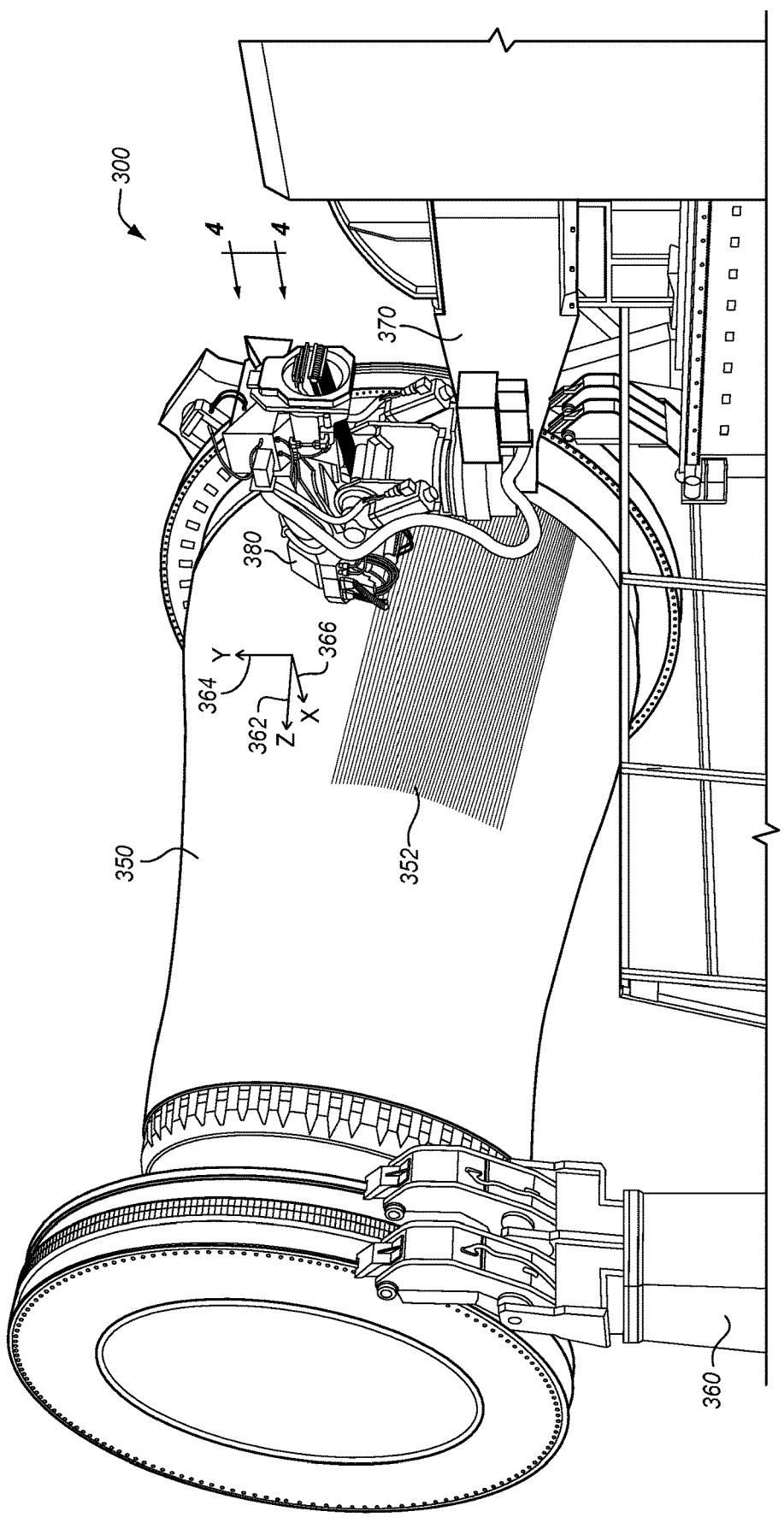
FIG. 3 is a diagram illustrating a tape layup machine in an illustrative embodiment.

FIG. 3 is a diagram illustrating a tape layup machine 300 that is mounted to a support 370 in an illustrative embodiment. Tape layup machine 300 comprises any system or device capable of laying up lanes 352 of tape that form a laminate 350 (e.g., for curing into a composite part). Tape layup machine 300 includes head 380, which dispenses lanes 352 of tape (e.g., CFRP) during layup. Lanes 352 are laid-up to form laminate 350, which comprises one or more layers of material that will be cured into a single monolithic composite part. In this embodiment, laminate 350 comprises a section for an aircraft, and is held in place by rotational holder 360.

As tape layup machine 300 operates to lay up the lanes 352 of tape onto laminate 350, tape layup machine 300 may move directly towards/away from laminate 350 along axis X 366, vertically upwards/downwards along axis Y 364, and/or laterally along axis Z 362. As used herein, when tape layup machine 300 lays up multiple lanes 352 concurrently during a single "sweep" of head 380, those lanes 352 are collectively referred to as a single "course." A set of non-overlapping courses that are applied consecutively may be referred to as a layer. As layers are added to laminate 350, the strength of the resulting composite part is increased.

Laying up material for a laminate 350 that is large (e.g., a section of fuselage) is a time-consuming and complex process. In order to ensure that lanes 352 are laid-up quickly and efficiently, the operations of tape layup machine 300 are controlled by an NC program. In one embodiment, the NC program provides instructions on a course-by-course basis for aligning/repositioning the tape layup machine 300, to control layup processes all the way down to the application of individual tows/tapes, moving the head 380, and laying up lanes 352 onto laminate 350. In this manner, by performing the instructions in the NC program, tape layup machine 300 fabricates a laminate (e.g., a laminate for curing into a composite part).

Figure 4:
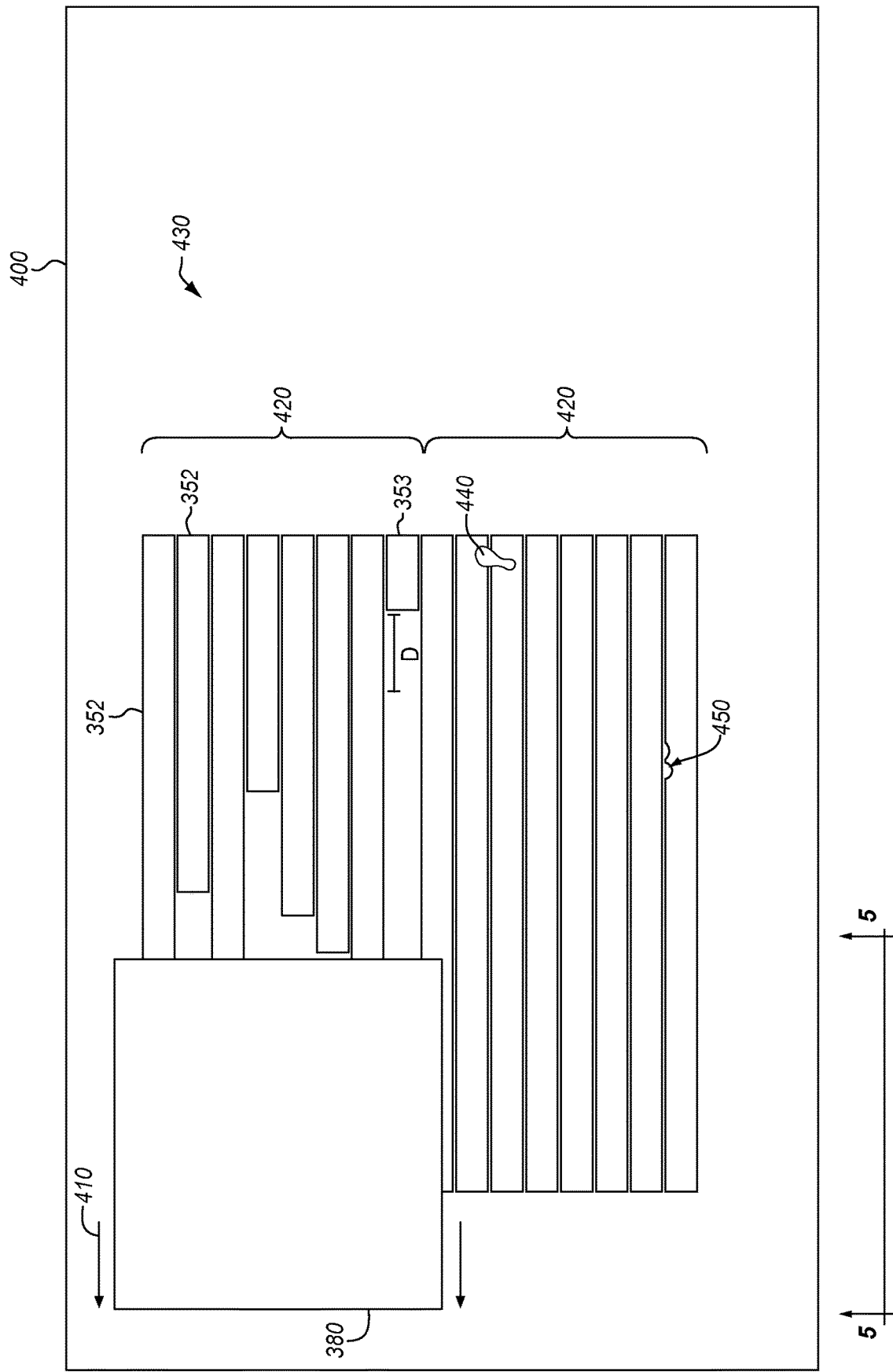
FIG. 4 is a top view of courses laid-up by a tape layup machine in an illustrative embodiment.

FIG. 4 is a top view of courses 420 laid-up by a tape layup machine in an illustrative embodiment, and corresponds with view arrows 4 of FIG. 3. FIG. 4 illustrates a laminate 400, which itself comprises lanes of tape that have been tacked together (not shown for clarity). As head 380 moves across surface 430 of laminate 400, it deposits a course 420 comprising one or more lanes 352 of tape onto the laminate 400. In this embodiment, each course comprises eight lanes of tows. For fiber reinforced laminates, each lane in a course will exhibit the same fiber direction, although different courses for different layers of the laminate may exhibit different fiber directions.

An NC program directing the head 380 may indicate locations at which to place each lane 352 within a course 420. However, the actual ends of the lanes 352 as placed onto the laminate 400 may vary. Thus, a distance D may exist between the actual end location of a lane 353, and the intended end location of the lane 353. Additionally, debris 440 may fall onto the laminate during or after layup, and one or more layup inconsistencies 450 may also occur during the layup process. Debris 440 may comprise pills or pulls of fiber at the tape ("fuzz balls"), liquids (e.g., oil or water), particles (e.g., metal shavings, granules of plastic material, etc.), and a backing for the tape. Layup inconsistency 450 may comprise a twisted tape, a folded tape, a bridging of tape, a pucker, a wrinkle, an untacked tow or portion thereof, a missing tow, a double tow, a split or damaged tow, missing material, or other conditions.

Because thermal imaging may be utilized to quantify aspects of various features such as the locations of ends of lanes, the locations of foreign debris, and the locations of layup inconsistencies, the time and labor spent reworking the laminate 400 is reduced. That is, because out of tolerance features of the laminate 400 are immediately detected during layup, only a section of a course will need to be dispositioned. Furthermore, because the laminate 400 remains green and uncured during the inspection process, the rebuilding process is a simple matter of directly removing and re-applying lanes of tape to the laminate. This is not possible after the laminate has been cured into a composite part.

Figure 5A:
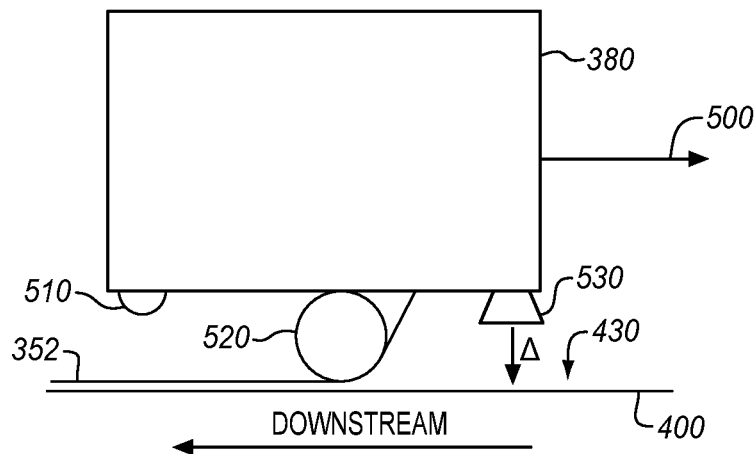
FIGS. 5A-5B, 6, and 7 are side views of heads of a tape layup machine in an illustrative embodiment.
Figure 5B:
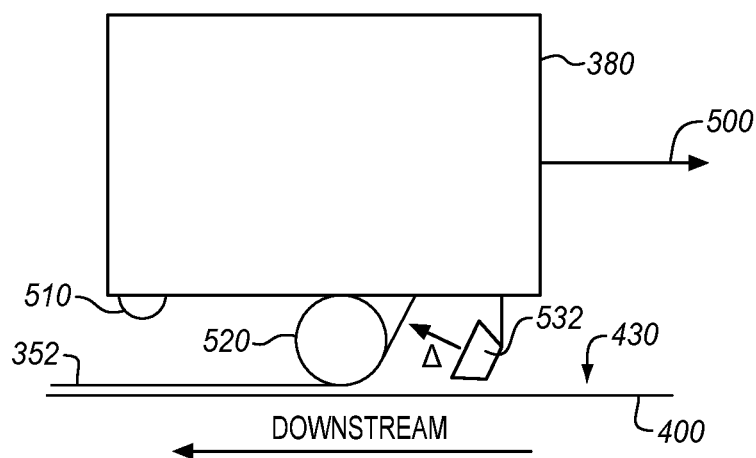
Figure 6:
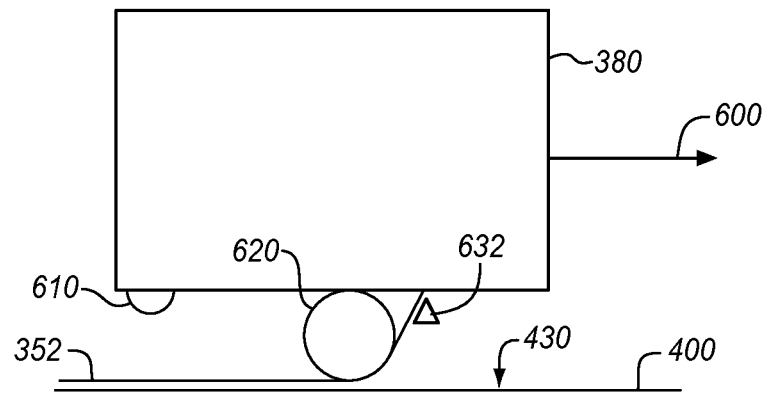
Figure 7:
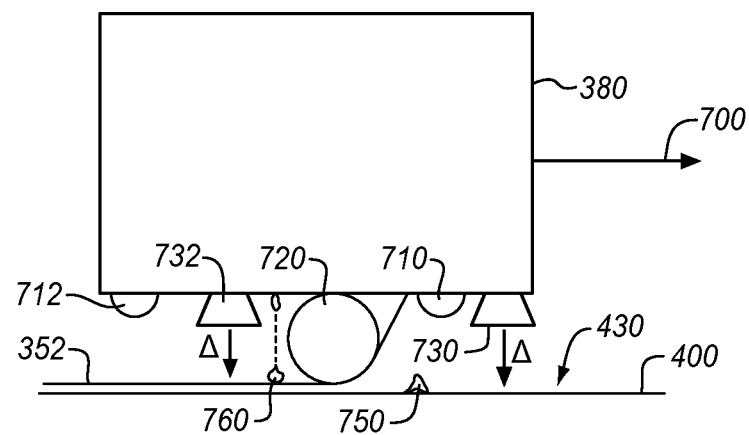

FIGS. 5-7 are side views of various configurations of a head 380 of a tape layup machine, and corresponds with view arrows 5 of FIG. 4. Specifically, FIGS. 5A-5B illustrate heads configured to inspect thermoset lanes of tape applied to laminates, FIG. 6 illustrates a head configured to inspect thermoplastic lanes of tape applied to laminates, and FIG. 7 illustrates a head configured to inspect a laminate for debris.

FIG. 5A is a side view of a head 380 for inspecting thermoset lanes of tape applied to laminates in an illustrative embodiment. As shown in FIG. 5A, head 380 proceeds in direction 500, and includes a compaction roller 520 for compacting lanes 352 of tape onto surface 430 of laminate 400. Heater 530 applies heat (Δ) to the surface 430, in order to increase the temperature of surface 430 to a temperature where it softens and becomes tacky (i.e., to increase tack for the layer that was previously laid-up and is about to be covered up by a new layer). Although heater 530 is shown as being a distance in front of compaction roller 520, in further embodiments the heater 530 is placed immediately in front of compaction roller 520. When lanes 352 are applied to surface 430, a temperature differential exists between the lanes and the underlying (e.g., unheated) laminate. This makes the lanes 352 distinguishable from the underlying laminate when reviewing thermographic images from IR camera 510, which trails (i.e., is located downstream of) compaction roller 520. FIG. 5B illustrates a further view wherein a heater 532 is disposed upstream of compaction roller 520, and heats tape for one or more lanes 352 prior to the tape reaching the compaction roller 520.

FIG. 6 is a side view of head 380 for inspecting thermoplastic lanes of tape applied to a laminate in an illustrative embodiment. As shown in FIG. 6, head 380 proceeds in direction 600, and includes a compaction roller 620 for compacting lanes 352 of tape onto surface 430 of laminate 400. A heater 632 applies targeted heat (Δ) to tape within lanes 352 in order to increase the temperature up to or in excess of the thermoplastic material melt temperature. This heat is applied at or just before tape for the lanes 352 is compacted onto laminated 400. This enables detection of added or lost lanes of tape, as well as debris. When tape for lanes 352 is applied to surface 430, a temperature differential exists between the lanes and the underlying laminate. This makes the lanes distinguishable from the underlying laminate when reviewing thermographic images from the IR camera 610, which trails compaction roller 620.

FIG. 7 is a side view of a head 380 for inspecting a laminate in order to detect debris in an illustrative embodiment. As shown in FIG. 7, head 380 proceeds in direction 700, and includes a compaction roller 720 for compacting lanes 352 of tape onto surface 430 of laminate 400. Head 380 also includes heater 730 and IR camera 710, as well as heater 732 and IR camera 712. Heater 730 applies heat (Δ) to the surface 430, in order to increase the temperature of surface 430. Debris 750 (e.g., Foreign Object Debris (FOD), a pill of fiber, etc.) located at surface 430 is therefore heated by heater 730. Because the underlying thermal properties of the debris are likely to vary from that of surface 430, or because the shape of the debris may alter its ability to retain heat as compared to surface 430 and/or because the shape of the debris may be recognizable via image analysis, the debris 750 may be detected in thermographic images acquired by IR camera 710.

Head 380 additionally includes heater 732 and IR camera 712. Heater 732 increases a temperature of lanes 352. This helps IR camera 712 to better distinguish between debris 760 (e.g., new debris falling off of head 380, such as oil) and the lanes 352. Thus, when debris exists on surface 430 before tape for one or more lanes 352 are laid-up, the debris can be detected by IR camera 710, while debris that lands on lanes 352 after the lanes 352 are laid-up can be detected by IR camera 712.

The arrangement depicted in FIG. 7 has an additional advantage in that the IR camera 732 may also indirectly detect debris 750. Debris 750 often conducts heat differently between lanes 352 and laminate surface 430 than does direct contact between lanes 352 and laminate surface 430. If debris 750 is more insulating (i.e., conducts heat worse) than direct contact, or debris 750 induces an air gap (which also insulates) between lanes 352 and laminate surface 430, then the area of one or more lanes 352 above the debris 750 will appear hotter than surrounding lanes, and this hot spot may be used as detection of debris 750 buried under lanes 352. If debris 750 is more conductive (i.e., conducts heat better) than direct contact between lanes 352 and laminate surface 430, then the area of lanes 352 which are above the debris 750 will appear colder than the surrounding lanes 352, and this cold spot may be used as detection of debris 750 buried under lanes 352.

FIGS. 8-13 illustrate various specific techniques for identifying ends of lanes of tape, layup inconsistencies, and debris respectively. Specifically, FIGS. 8-9 describe identifying the ends of lanes of tape, FIGS. 10-11 describe identifying layup inconsistencies, and FIGS. 12-13 describe identifying debris.

Figure 8:
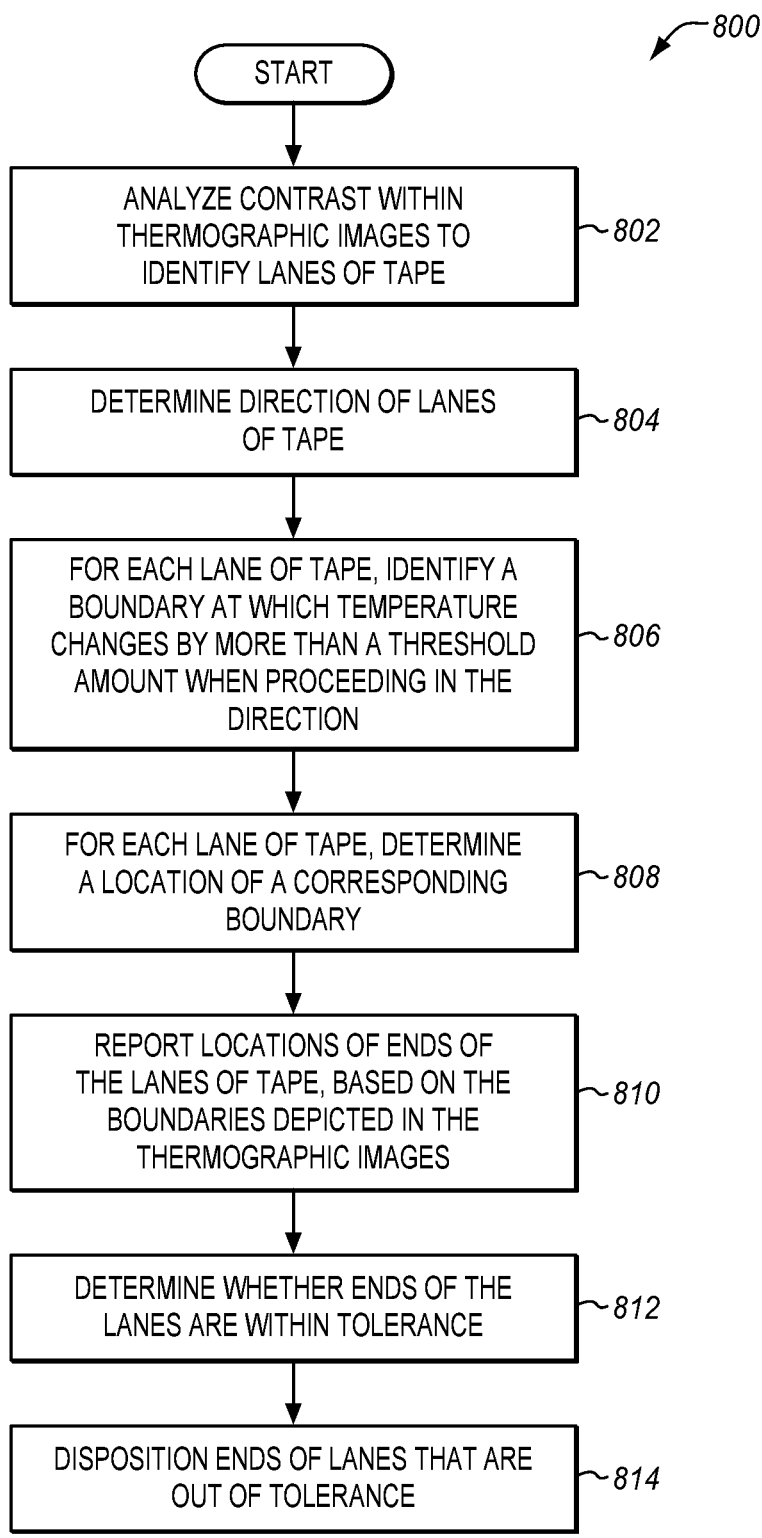
FIG. 8 is a flowchart illustrating a method for determining locations of ends of lanes of tape based on a thermographic image in an illustrative embodiment.

FIG. 8 is a flowchart illustrating a method 800 for operating a tape layup inspection system to detect ends of lanes of tape in an illustrative embodiment. The steps of method 800 are described with respect to tape layup inspection system 100 of FIG. 1, and may be performed via the head 380 depicted in FIG. 5 or FIG. 6, or even the head 380 depicted in FIG. 7. Method 800 may initiate with steps 202-206 of method 200 described above, to lay up and image lanes of tape at a laminate.

In step 802, controller 112 analyzes contrast within thermographic images 118 to identify lanes 160 of tape 154. Controller 112 may identify values (e.g. intensity levels, or brightness levels) at each of multiple pixels within the thermographic images 118. Pixel values within the thermographic images correspond with temperatures. Hence, controller 112 may identify regions that have different temperatures, based on differences between values of neighboring pixels.

This process may include identifying contiguous regions of pixels that have a temperature differential of more than a predetermined threshold amount with respect to neighboring contiguous regions of pixels, or grouping all contiguous pixels that are within a threshold range of temperatures (e.g., five degrees Fahrenheit, fifty degrees Fahrenheit) together with each other into a region. For example, if the lanes 160 of tape 154 are known to have a temperature differential between one and fifty degrees Fahrenheit with respect to the laminate 150, controller 112 may identify contiguous regions of pixels that have a corresponding temperature differential to surrounding regions as being lanes of tape.

In step 804, controller 112 determines a direction of the lanes 160 of tape 154. The direction of a lane of tape is the direction in which head 140 moves while laying up the lane. The direction may be predefined based on a known orientation of the camera with respect to the head 140, considered in combination with position data 120 and/or directions specified by the NC program 135. Controller 112 may even use position data 120 to confirm that the head 140 moves in a direction indicated by NC program 135. Alternatively, the direction or may be dynamically determined based on the longest axis found for lanes depicted within a thermographic image.

In step 806, for each lane of tape, controller 112 identifies a boundary at which temperature changes by more than a threshold amount when proceeding in the direction determined in step 804. That is, within the bounds of each lane of tape, controller 112 reviews the values of adjacent/neighboring pixels, while moving pixel-by-pixel in the direction until a boundary is detected. The threshold amount used for boundary detection may vary between thermoset and thermoplastic materials, as discussed above. In some embodiments, step 806 may comprise running an edge detection algorithm (e.g., applying a Laplacian or other filter) to the thermographic image 118, and identifying regions where a sharp transition between temperatures occurs.

In step 808, controller 112 determines a location of a corresponding boundary for each of the lanes 160 of tape 154. This may comprise transforming coordinates at the thermographic image 118 into locations at the laminate 150, for example, based upon a known position and/or orientation of an IR camera at the time that the IR camera generated the thermal image, and a known offset between the IR camera and coordinates of pixels.

In step 810, controller 112 reports locations of the ends of the lanes 160 of tape 154, based on the boundaries detected in the thermographic images. For example, controller 112 may report the locations determined in step 808, in either a textual report or an overlay provided atop an image of the laminate 150. If the locations of the ends of the lanes 160 are more than a threshold amount (e.g., one inch, ten inches, etc.) from their intended start locations and stop locations, controller 112 may indicate this condition as part of the report. In step 812, controller 112 determines whether the ends of the lanes are within tolerance. If any of the ends of the lanes are out of tolerance, step 814 comprises dispositioning these ends. Dispositioning may include any type of determination of the course of action to deal with a discovered out of tolerance condition for an end.

Figure 9:
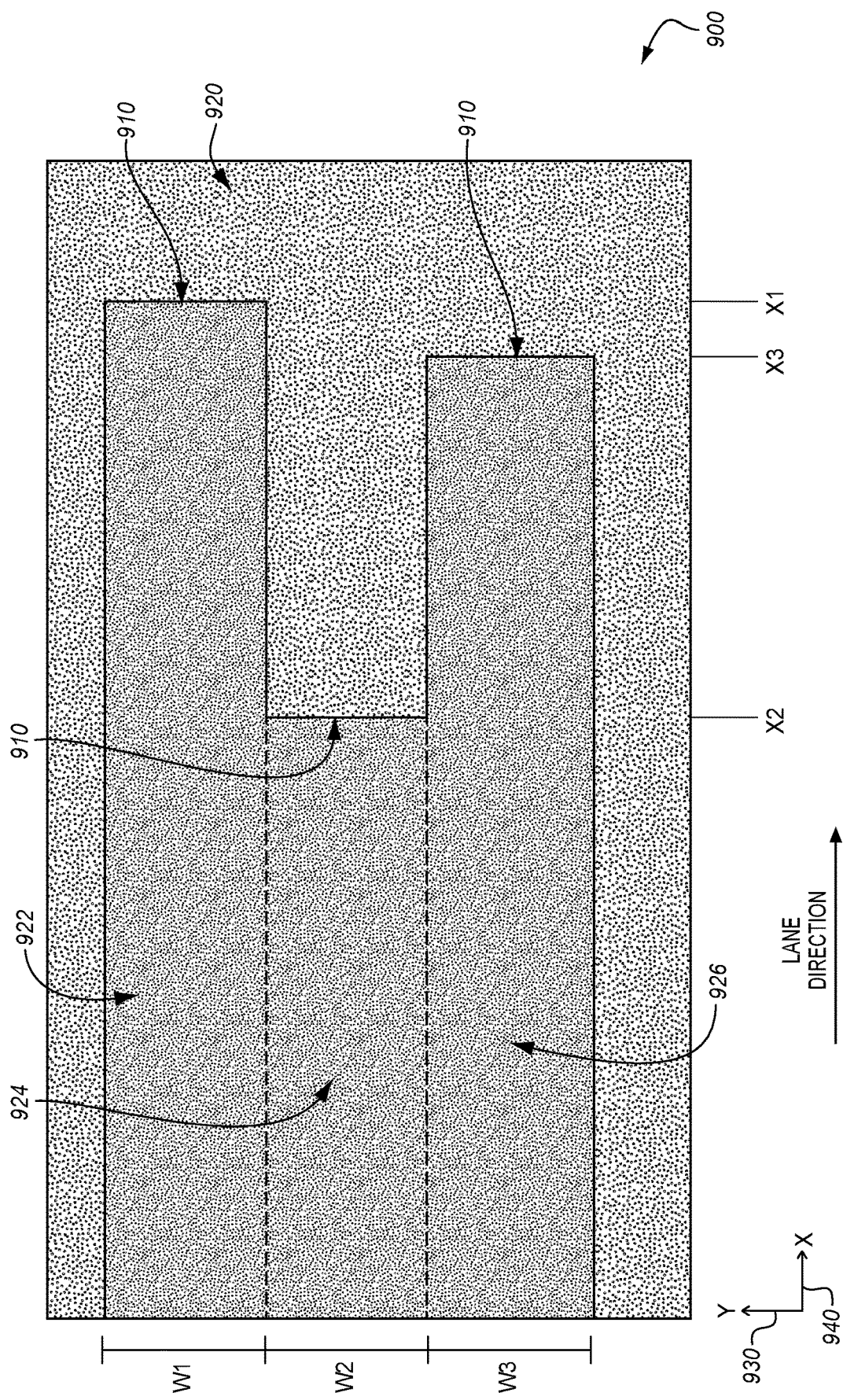
FIG. 9 is a thermographic image of a portion of a course that includes ends of lanes of tape in an illustrative embodiment.

FIG. 9 is a thermographic image 900 of a portion of a course in an illustrative embodiment. Within the thermographic image, pixels that represent objects having different temperatures will have different values (e.g., levels of brightness). Thus, a pixel for a cool object may appear darker than a pixel for a warm object. Controller 112 may analyze thermographic image 900 by applying an edge-detection algorithm, or otherwise searching for transitions in temperature along the Y direction 930 that are greater than a threshold amount (e.g., greater than one degree Fahrenheit). Controller 112 may then determine a location and thickness of each lane depicted within the thermographic image 900. Fibers may be oriented in any suitable direction within each of the lanes of tape. For example, a region 922 depicting a top lane has a width W1, a region 924 depicting a middle lane has a width W2, and a region 926 depicting bottom lane has a width W3. These regions are surrounded by region 920, which represents the underlying laminate (as determined by differences in temperature). Within the Y coordinates occupied by each lane, controller 112 may traverse pixels in the X direction 940 to identify boundaries 910 between pixels that are greater than the threshold. For each boundary 910 identified in this manner, controller 112 may identify the X and Y coordinate of the boundary 910 within the image as the end of a lane. For example, the top lane ends at X1, the middle lane ends at X2, and the bottom lane ends at X3. In embodiments where the boundaries comprise regions of pixels, controller 112 may calculate a centroid of the region, and use the coordinate of the centroid. The coordinates may be transformed into locations at the laminate 150 based on position data 120, and the locations may be compared against desired locations indicated in an NC program. If the locations are more than a threshold distance (e.g., one foot, one inch, etc.) from the desired locations, then a technician may elect to pause layup processes for the laminate, in order to disposition (e.g., rework) any out-of-tolerance conditions. In addition, a statistical report may be provided to the technician that compares desired lane locations to the identified lane locations for each layer.

Figure 10:
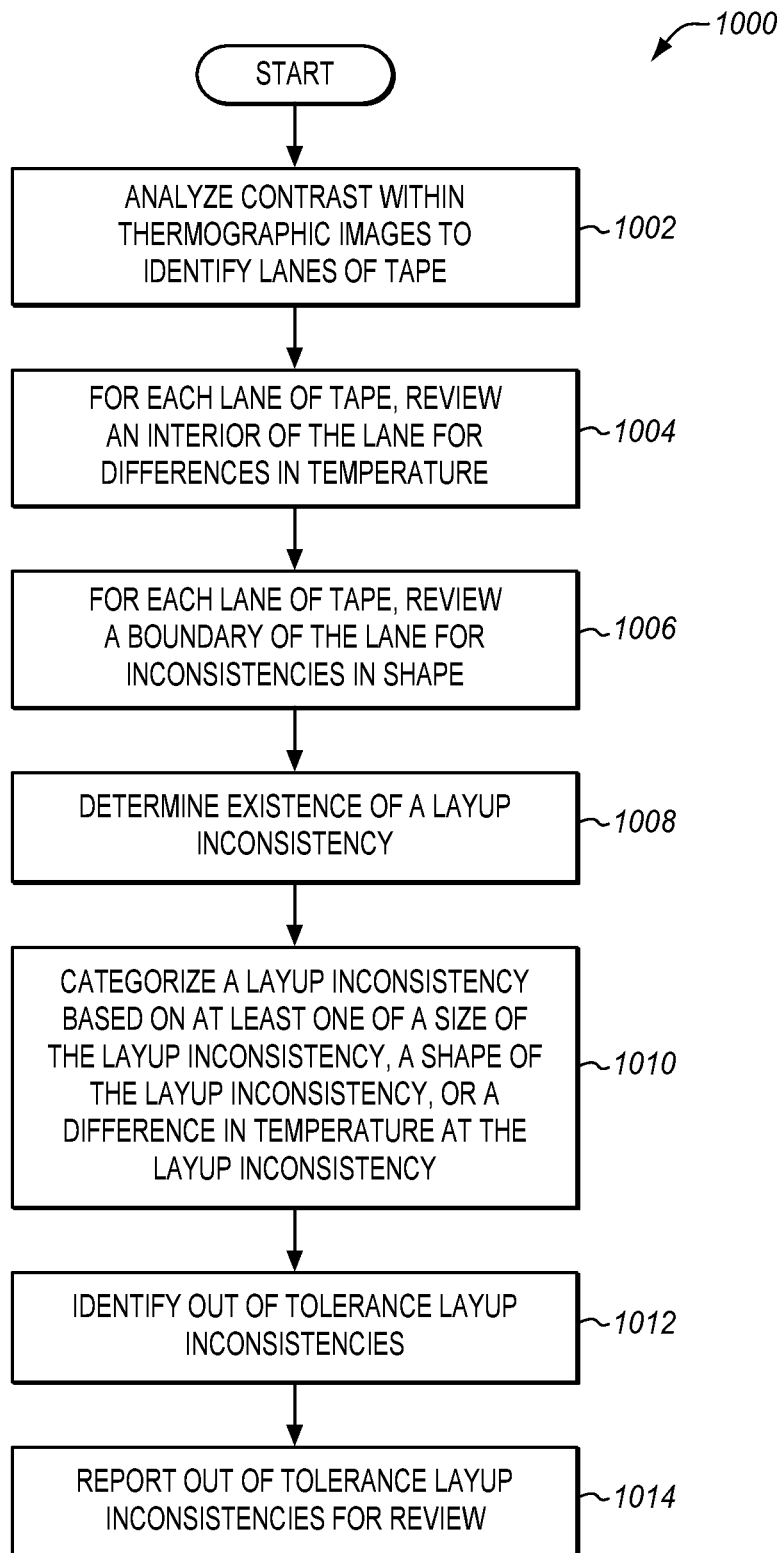
FIG. 10 is a flowchart illustrating a method for detecting layup inconsistencies in an illustrative embodiment.

FIG. 10 is a flowchart illustrating a method 1000 for detecting layup inconsistencies in an illustrative embodiment. The steps of method 1000 are described with respect to tape layup inspection system 100 of FIG. 1, and may be performed via the head 380 depicted in FIG. 5 or FIG. 6, or even the head 380 depicted in FIG. 7. Method 1000 may initiate with steps 202-206 of method 200 described above, to lay up and image lanes of tape at a laminate.

Step 1002 includes analyzing contrast within thermographic images 118 to identify lanes 160 of tape 154. This may be performed based on an expected amount of temperature difference between the laminate 150 and the lanes 160, and may be performed in a similar manner to the steps of method 800 provided above.

In step 1004, for each lane of tape, controller 112 reviews an interior of the lane for differences in temperature. These differences in temperature may be low enough that the interior of the lane is not considered a different region, but may be high enough (to indicate that a inconsistency may exist. Step 1004 therefore facilitates detection of layup inconsistencies found within a lane of tape.

In step 1006, for each lane of tape, controller 112 reviews a boundary of the lane for inconsistencies in shape. For example, lanes may be expected to have boundaries that are roughly rectangular in shape, and are composed of long straight lines. If a boundary exhibits a high curvature or irregularity, this may indicate the presence of a layup inconsistency. Step 1006 therefore facilitates detection of layup inconsistencies found at the edge of one or more lanes of tape.

In step 1008, controller 112 determines the existence of a layup inconsistency, for example based upon the reviews of step 1004 and step 1006. In step 1010, controller 112 categorizes the layup inconsistency based on at least one of a size of the layup inconsistency, a shape of the layup inconsistency, or a difference in temperature at the layup inconsistency. For example, detection functions 122 may indicate that a inconsistency exists if the width of a tow changes to less than a predetermined amount, if a gap between tows increases beyond or decreases below a threshold value, if a boundary of a tow is jagged, etc. Different ones of detection functions 122 may be triggered (and hence different categories of inconsistency may be assigned by controller 112) based on various combinations of shape, size, and temperature. In step 1012, controller 112 identifies out-of-tolerance layup inconsistencies, and in step 1014, controller 112 reports out of tolerance layup inconsistencies for review (e.g., in order to enable a technician to engage in dispositioning of the out of tolerance conditions.

Figure 11:
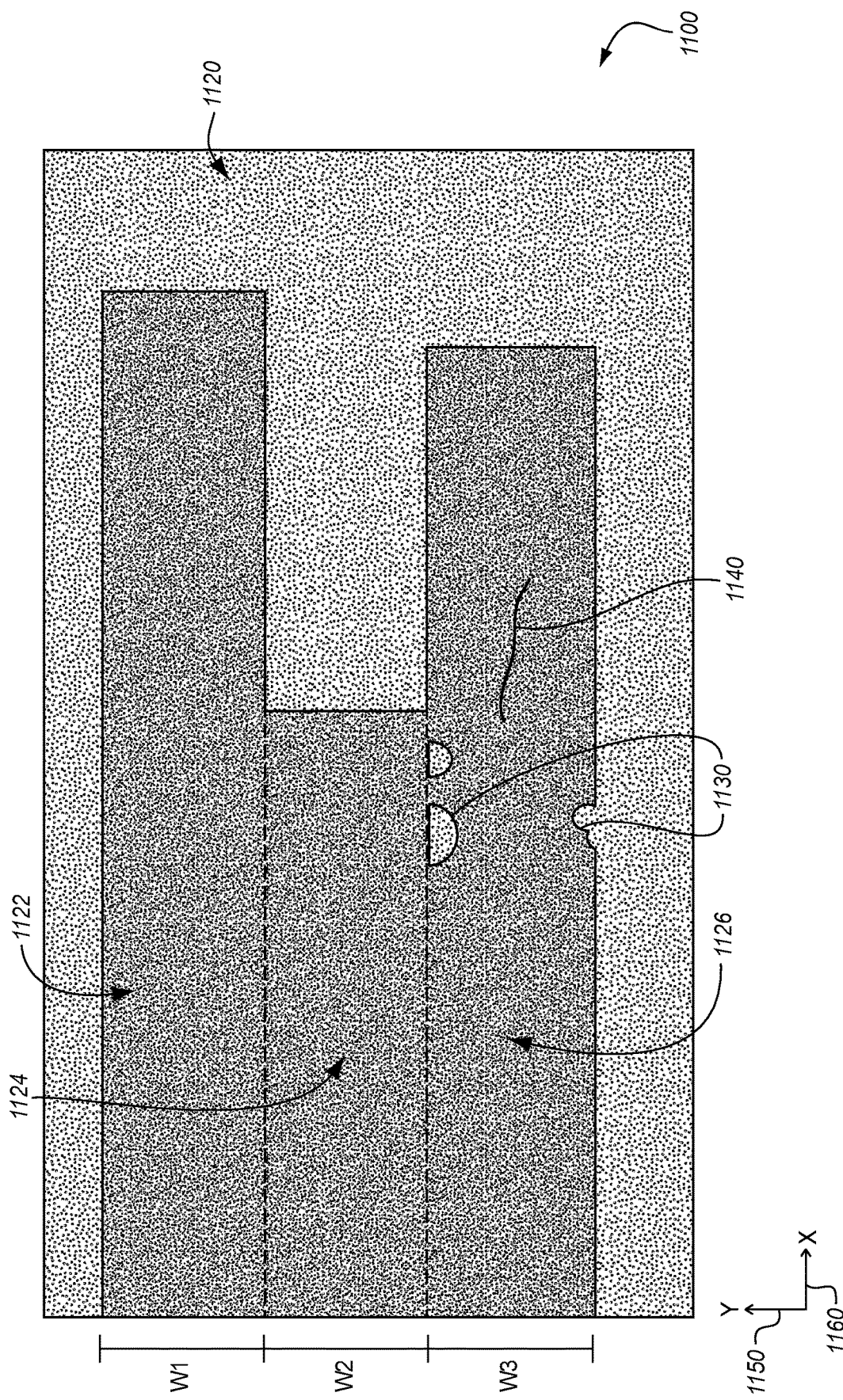
FIG. 11 is a thermographic image of a portion of a course that includes a layup inconsistency in an illustrative embodiment.

FIG. 11 is a thermographic image 1100 of a portion of a course that includes layup inconsistencies in an illustrative embodiment. Within the thermographic image, pixels that represent objects having different temperatures will have different values (e.g., levels of brightness). Thus, a pixel for a cool object may appear darker than a pixel for a warm object. The lanes have a length along the X direction 1160, and width along the Y direction 1150. In this embodiment, lanes 1122 and 1124 do not include inconsistencies, while lane 1126 includes layup inconsistencies 1130 in the form of a pucker, and layup inconsistency 1140 in the form of a wrinkle. Layup inconsistencies 1130 may be determined based on lane 1126 dropping below an expected width or having a varying width, or may be detected by determining that a curvature of the edge of lane 1126 changes or is within a predefined range. Layup inconsistencies may also be detected by temperature differences (beyond a threshold) between lane 1126 and an underlying layer 1120 of the laminate. Meanwhile, layup inconsistency 1140 may be detected based on its long, narrow shape, and having a known temperature difference with respect to the rest of the lane 1126.

Figure 12:
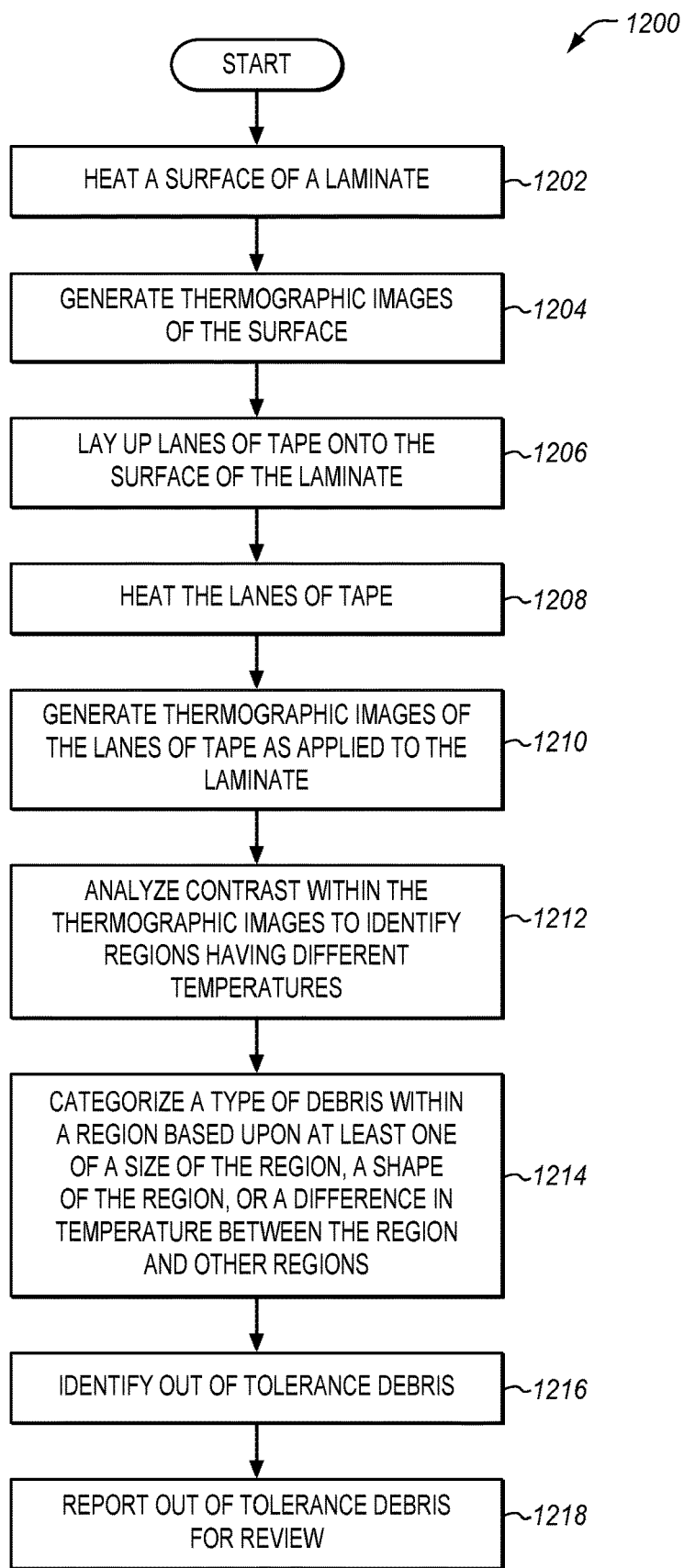
FIG. 12 is a flowchart illustrating a method for determining locations of debris based on a thermographic image in an illustrative embodiment.

FIG. 12 is a flowchart illustrating a method 1200 for determining locations of debris based on a thermographic image in an illustrative embodiment, and may be performed via the head 380 depicted in FIG. 7. The steps of method 1200 are described with respect to tape layup inspection system 100 of FIG. 1, but may be performed in other systems as desired. Method 1200 includes heating a surface 156 of laminate 150 via heater 141 in step 1202, and generating thermographic images 118 of the surface 156 via IR camera 142 in step 1204. Method 1200 also includes laying up lanes 160 of tape 154 onto the surface 156 of laminate 150 via tape dispensers 143 in step 1206. In step 1208, method 1200 includes heating the lanes 160 of tape 154 via heater 144, and step 1210 includes generating thermographic images of the lanes 160 of tape 154 as applied to the laminate 150. Ideally, the lanes 160 are heated to the same temperature as the laminate 150. This enables debris (e.g., FOD) to be more easily distinguished from the tape 154 that lanes 160 and laminate 150 are made from.

Having acquired the thermographic images 118 depicting both the laminate 150 and the lanes 160 applied to the laminate 150, foreign object debris can be spotted accurately and efficiently by identifying differences in temperature. In step 1212, controller 112 analyzes contrast within the thermographic images to identify different regions having different temperatures, which may be performed in a similar manner to the techniques described above. However, because different categories of debris may be associated with substantially different thermal properties, regions may be distinguished based on a variety of different temperature thresholds, each corresponding to a different type of debris. For example, pills of fiber at the tape may be expected to be a first range of temperatures higher than the underlying laminate, to be small in size and to have irregular borders, while liquids may be expected to be a second range of temperatures cooler than the underlying laminate, have a wide range of sizes, and have smooth borders. Thus, the amount of temperature difference used as criteria to define separate regions in method 1200 (e.g., less than five degrees, less than two degrees, etc.) may be much smaller than the amount of temperature difference described with respect to other methods.

Because thermographic images are acquired both before and after laying up lanes of tape, analyzing contrast within the thermographic images may comprise reviewing the thermographic images of the surface of the laminate to identify debris covered by at least one layer of tape, and also reviewing the thermographic images of the lanes of tape as applied to the laminate to identify debris at a surface of the lanes of tape. The process may even be stopped prior to laying up a course over an out of tolerance piece of debris detected by IR camera 710. This allows disposition (e.g. removal of the piece of debris) prior to applying the course over the debris. If the debris is not out of tolerance, applying a course over it might be a desired action. To facilitate detection of debris at boundaries between lanes or courses, images may have a wide enough field of view to capture likely locations at which the debris will be located.

In step 1214, controller 112 categorizes a type of debris within a region based upon at least one of a size of the region, a shape of the region, or a difference in temperature between the region and other regions. For example, pills of fiber may be expected to have irregular shapes, to have a specific amount of temperature differential from the underlying laminate, and to be small (e.g., having a maximum number of pixels corresponding with an area of less than a centimeter across). Particles such as metal shavings may be expected to be particularly small or a different temperature than their surroundings, and liquids may be expected to be have a different range of temperature differentials with their surroundings, and also to have rounded borders. Furthermore, in some embodiments metal shavings of any size are considered out of tolerance, while pills below a certain size might be considered within tolerance. Detection functions 122 may indicate conditions for categorizing each of a variety of regions at a laminate into categories of debris. After debris has been categorized and identified by controller 112, controller 112 may generate a report indicating the nature, location, and/or severity of the debris that was detected. In step 1216, debris that is out of tolerance is identified (e.g., based on its size and classification) by controller 112, and in step 1218, out of tolerance debris is reported to a technician for dispositioning (e.g., removal).

Figure 13:
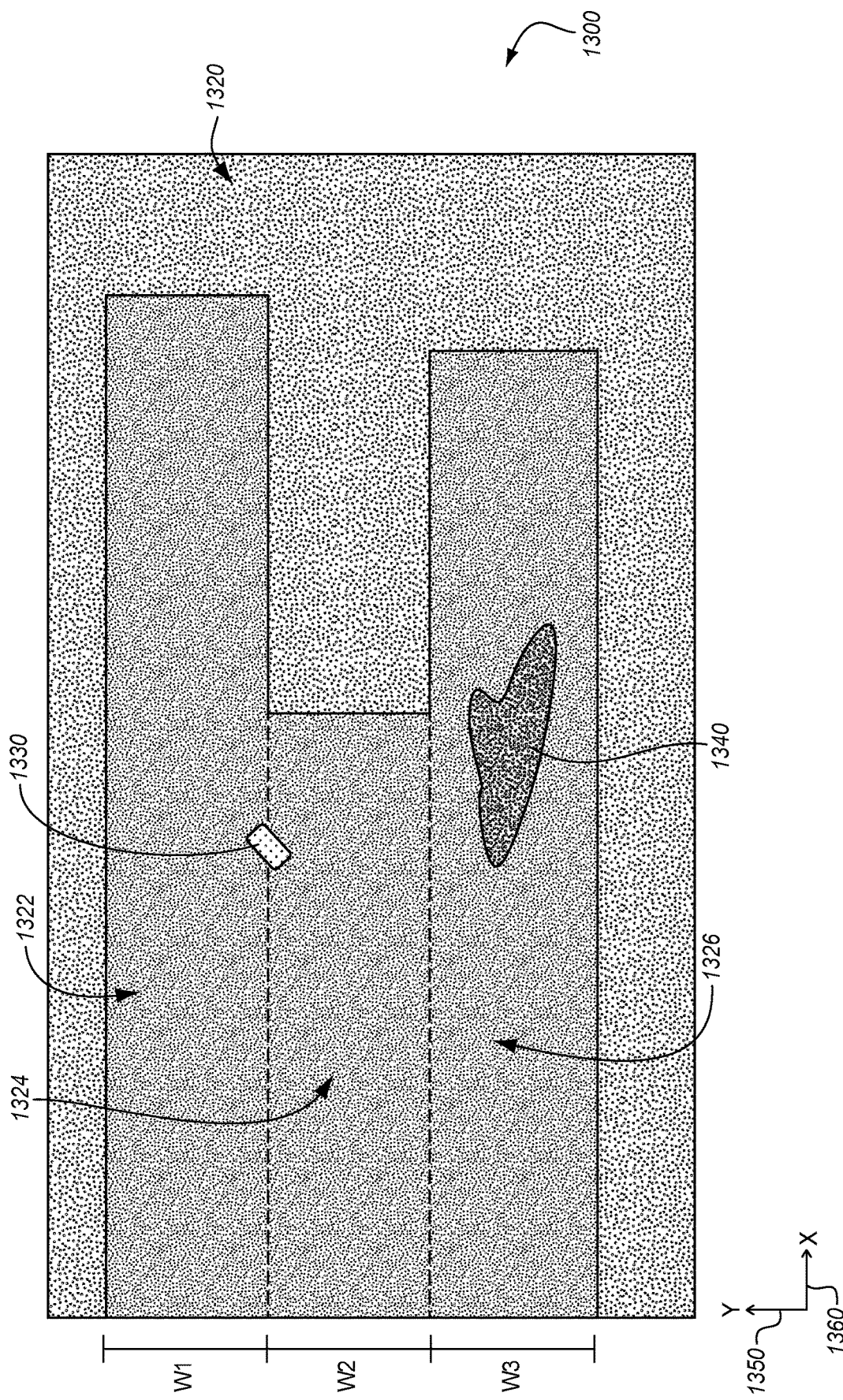
FIG. 13 is a thermographic image of a portion of a course that includes debris in an illustrative embodiment.

FIG. 13 is a thermographic image 1300 of a portion of a course that includes debris in an illustrative embodiment. Within the thermographic image, pixels that represent objects having different temperatures will have different values (e.g., levels of brightness). Thus, a pixel for a cool object may appear darker than a pixel for a warm object. In this embodiment, the course includes lane 1322, lane 1324, and lane 1326. Lane 1322 includes debris in the form of a metal pellet 1330 that happens to be hotter than its surroundings, and lane 1326 includes debris in the form of a liquid puddle 1340 that happens to be cooler than its surroundings. In this case, the metal pellet 1330 straddles a boundary of lane 1322 and an underlying laminate 1320. The courses proceed In the X direction 1360, and have a width along the Y direction 1350.

Figure 14:
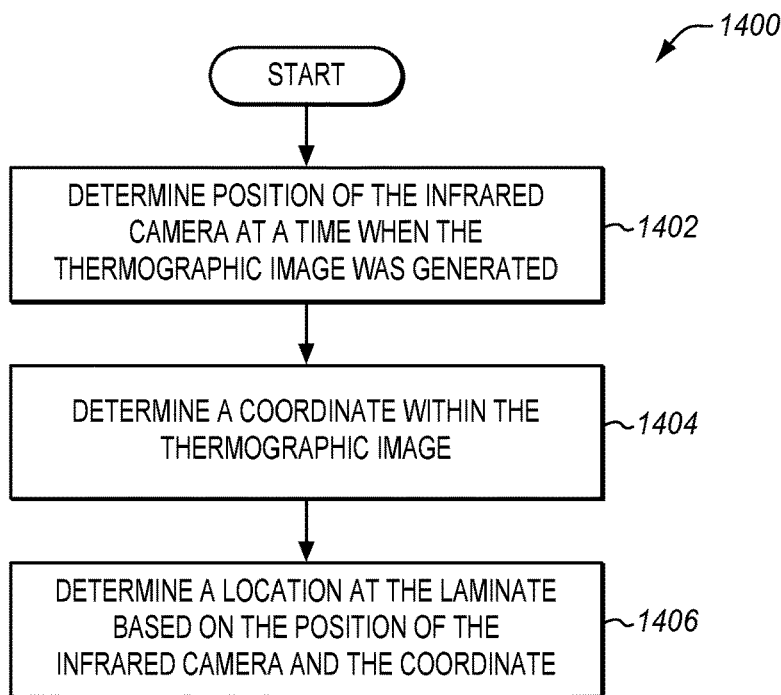
FIG. 14 is a flowchart illustrating a method of correlating image coordinates with physical locations in an illustrative embodiment.

FIG. 14 is a flowchart illustrating a method 1400 of correlating image coordinates with physical locations in an illustrative embodiment. In step 1402 of method 1400, controller 1412 determines a position and/or orientation of an IR camera 145 at the time when a thermographic image was generated by the IR camera 145. This may come in the form of position data 120 reported by position sensors 139 of FIG. 1. In step 1404, controller 112 determines a coordinate (e.g., an X and Y position) of a feature depicted within the thermographic image. This may comprise identifying a region having a different temperature than neighboring regions, and calculating a centroid of the region.

Step 1406 includes determining a location at the laminate based on the position of the IR camera 145 and the coordinate of the feature. For example, position data may indicate a position and orientation of the IR camera 145 when the thermographic image was taken. Because the camera is fixed with respect to a head of a tape layup machine, each coordinate within all images may correspond with a known physical offset from the IR camera 145. Hence, by applying the offset, the actual location of a feature at the laminate can be reliably determined.

Figure 15:
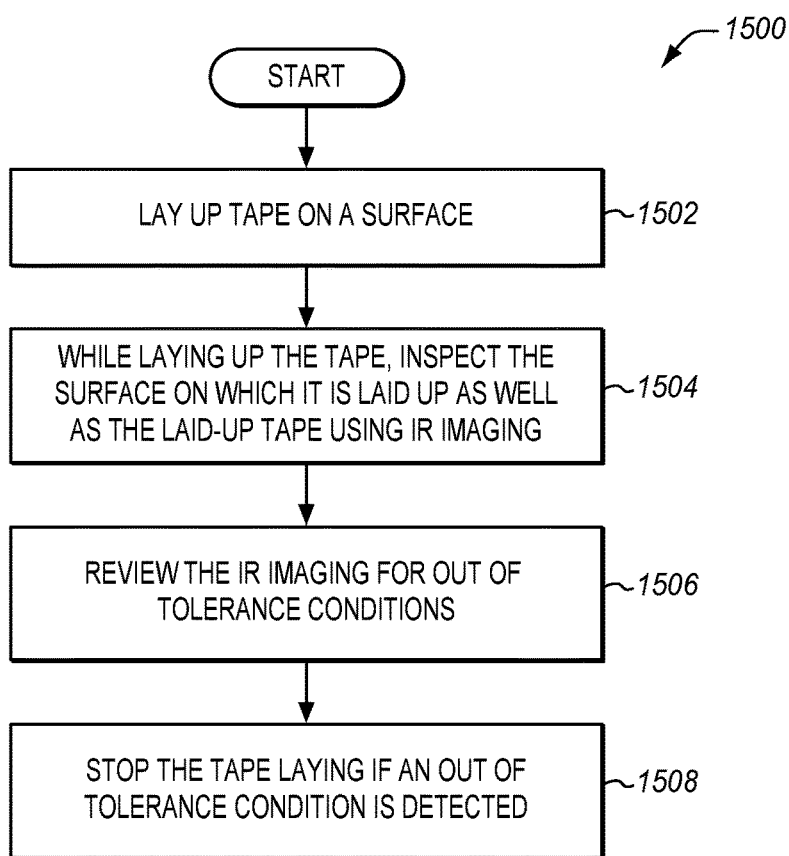
FIGS. 15-18 illustrate further methods pertaining to thermographic inspection in illustrative embodiments.

FIG. 15 illustrates a method 1500 of controlling a tape laying process in an illustrative embodiment. The method includes laying up tape on surface (step 1502), and while laying up the tape, inspecting the surface on which it is laid up as well as the laid up tape using IR imaging (step 1504). The method further comprises reviewing the IR imaging for out of tolerance conditions, and stopping the tape laying if an out of tolerance condition is detected (step 1508).

Figure 16:
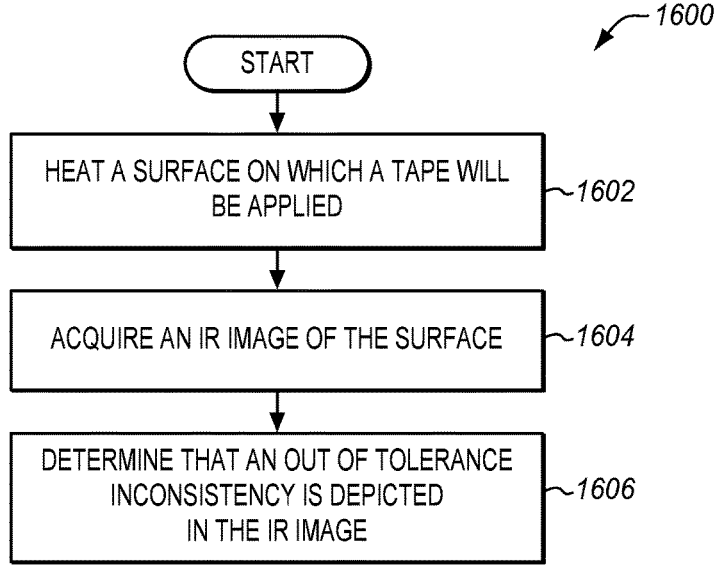

FIG. 16 illustrates a method 1600 of detecting out of tolerance inconsistencies during a tape laying process in an illustrative embodiment. The method includes heating a surface on which a tape will be applied (step 1602), acquiring an IR image of the surface (step 1604), and determining that an out of tolerance inconsistency is depicted in the IR image (step 1606).

Figure 17:
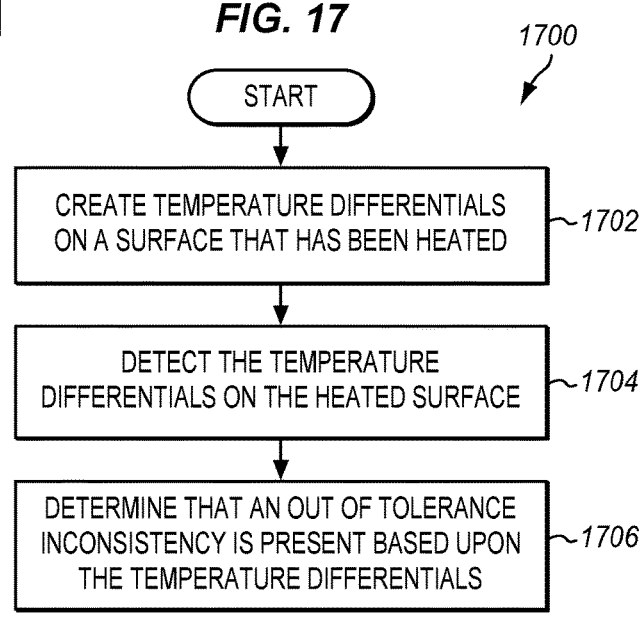

FIG. 17 illustrates a method 1700 of inspecting a composite surface in an illustrative embodiment. Method 1700 includes creating temperature differentials on a surface that has been heated (step 1702), detecting the temperature differentials on the surface (step 1704), and determining that an out of tolerance inconsistency is present based upon the temperature differentials (step 1706).

Figure 18:
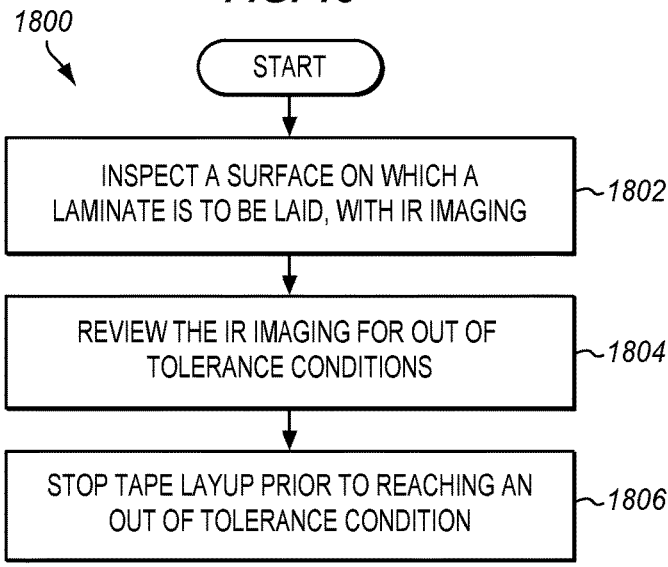

FIG. 18 illustrates a method 1800 of creating a composite structure in an illustrative embodiment. The method includes inspecting a surface on which a laminate is to be laid (step 1802), with IR imaging. The method also includes reviewing the IR imaging for out of tolerance conditions (step 1804) and stopping tape layup prior to reaching an out of tolerance condition (step 1806).

Figure 19A:
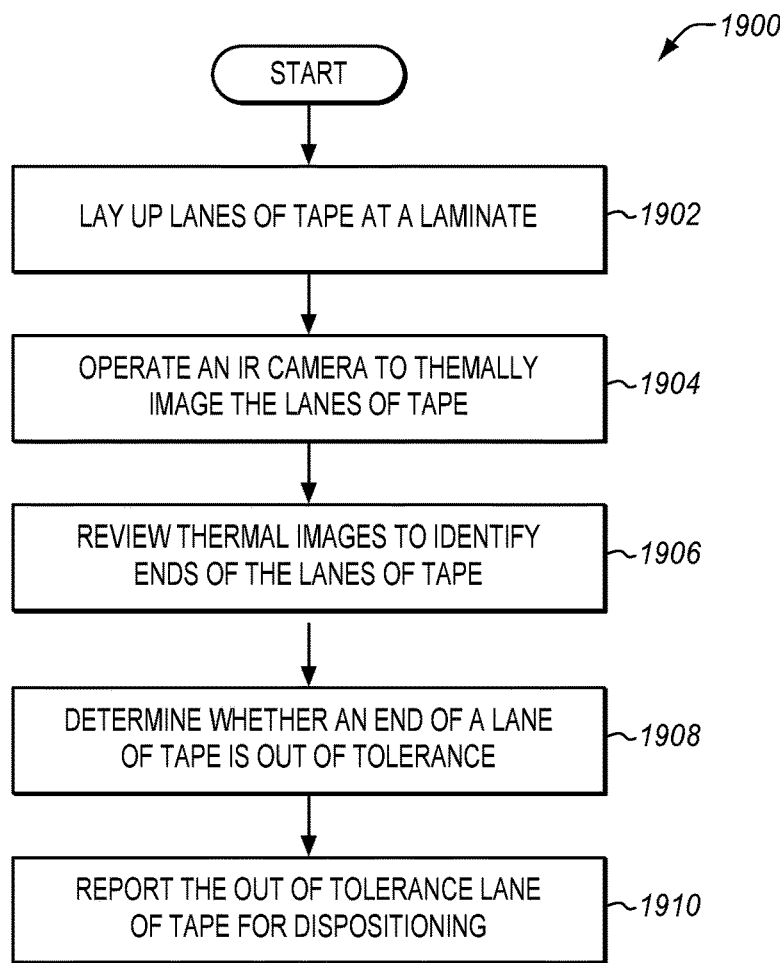
FIGS. 19A-19B illustrate further methods pertaining to thermographic inspection in illustrative embodiments.
Figure 19B:
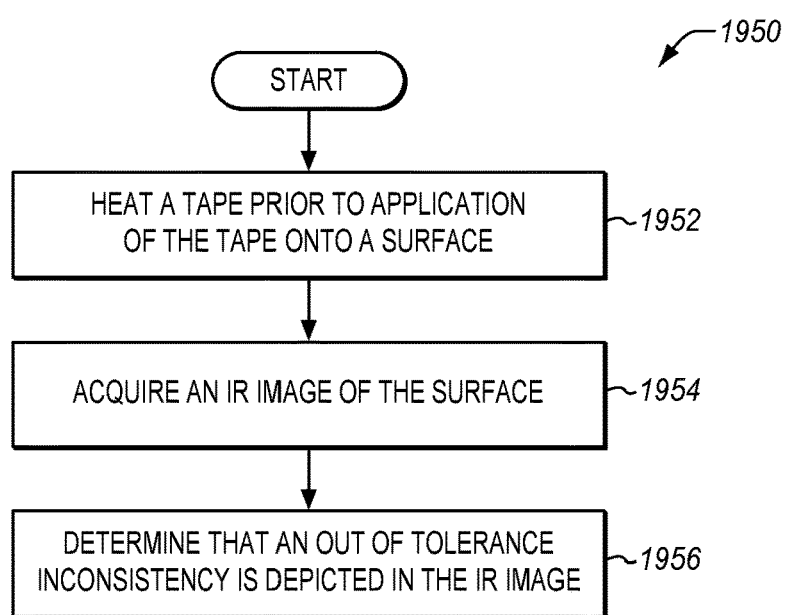

FIGS. 19A-19B illustrate methods 1900 and 1950 of inspecting tape end layup in an illustrative embodiment. Method 1900 includes laying up lanes of tape at a laminate (step 1902), operating an IR camera to thermally image the lanes of tape (step 1904), reviewing thermal images to identify ends of the lanes of tape (step 1906), determining whether an end of a lane of tape is out of tolerance (step 1908), and reporting the out of tolerance lane of tape for dispositioning (step 1910).

FIG. 19B illustrates method 1950 for inspecting tape end layup. Method 1950 if focused upon heating the tape prior to placing the tape, in order to improve tack. Method 1950 may be used to detect out of tolerance inconsistencies during a tape laying process in an illustrative embodiment. The method includes heating tape prior to application of the tape onto a surface (step 1952), acquiring an IR image of the surface (step 1954), and determining that an out of tolerance inconsistency is depicted in the IR image (step 1956).

EXAMPLES

Figure 20:
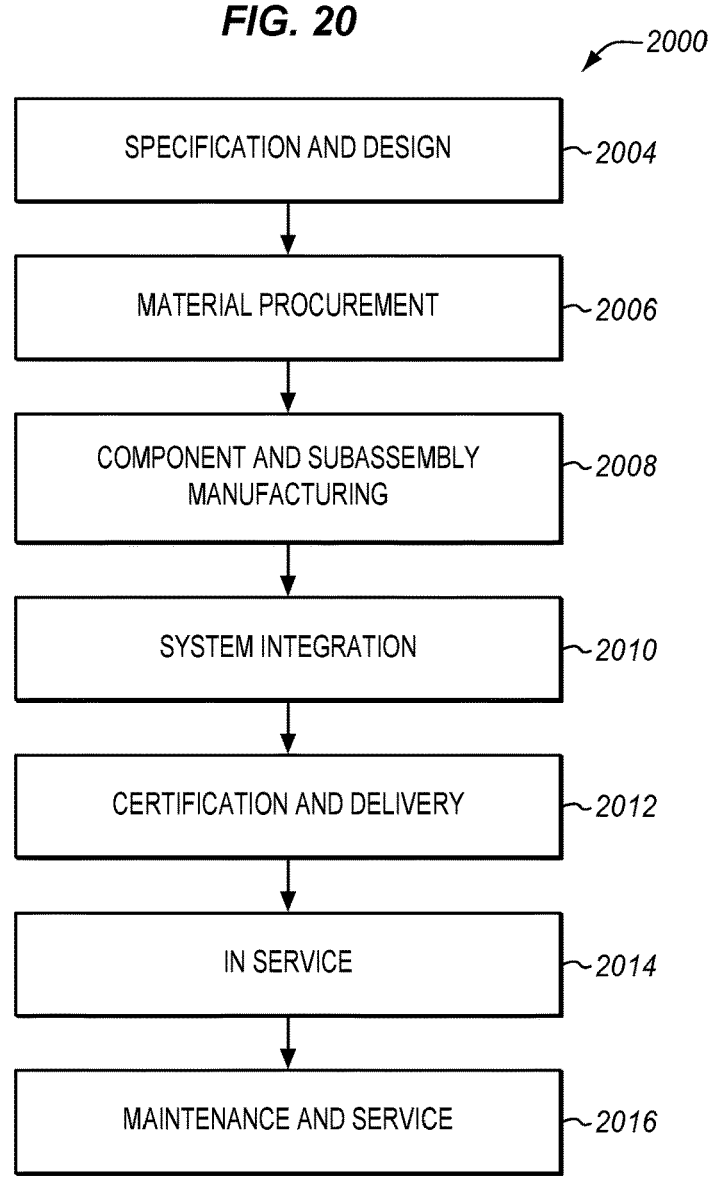
FIG. 20 is a flow diagram of aircraft production and service methodology in an illustrative embodiment.
Figure 21:
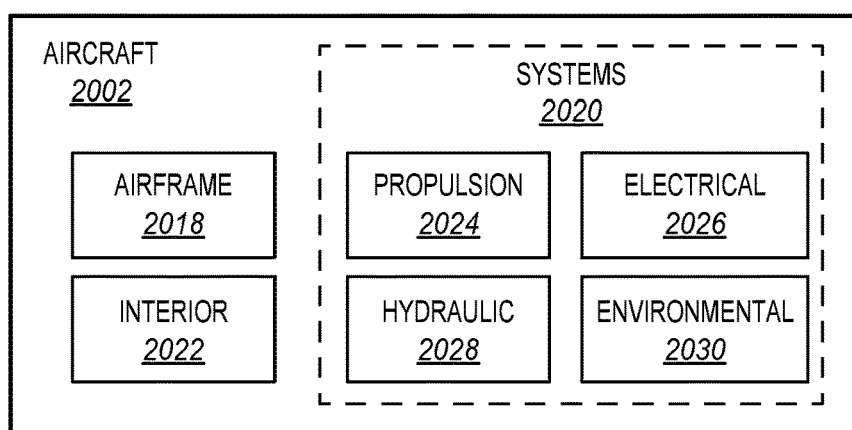
FIG. 21 is a block diagram of an aircraft in an illustrative embodiment.

Referring more particularly to the drawings, embodiments of the disclosure may be described in the context of aircraft manufacturing and service in method 2000 as shown in FIG. 20 and an aircraft 2002 as shown in FIG. 21. During pre-production, method 2000 may include specification and design 2004 of the aircraft 2002 and material procurement 2006. During production, component and subassembly manufacturing 2008 and system integration 2010 of the aircraft 2002 takes place. Thereafter, the aircraft 2002 may go through certification and delivery 2012 in order to be placed in service 2014. While in service by a customer, the aircraft 2002 is scheduled for routine work in maintenance and service 2016 (which may also include modification, reconfiguration, refurbishment, and so on). Apparatus and methods embodied herein may be employed during any one or more suitable stages of the production and service described in method 2000 (e.g., specification and design 2004, material procurement 2006, component and subassembly manufacturing 2008, system integration 2010, certification and delivery 2012, service 2014, maintenance and service 2016) and/or any suitable component of aircraft 2002 (e.g., airframe 2018, systems 2020, interior 2022, propulsion system 2024, electrical system 2026, hydraulic system 2028, environmental 2030).

Each of the processes of method 2000 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 21, the aircraft 2002 produced by method 2000 may include an airframe 2018 with a plurality of systems 2020 and an interior 2022. Examples of systems 2020 include one or more of a propulsion system 2024, an electrical system 2026, a hydraulic system 2028, and an environmental system 2030. Any number of other systems may be included. Although an aerospace example is shown, the principles of the invention may be applied to other industries, such as the automotive industry.

As already mentioned above, apparatus and methods embodied herein may be employed during any one or more of the stages of the production and service described in method 2000. For example, components or subassemblies corresponding to component and subassembly manufacturing 2008 may be fabricated or manufactured in a manner similar to components or subassemblies produced while the aircraft 2002 is in service. Also, one or more apparatus embodiments, method embodiments, or a combination thereof may be utilized during the subassembly manufacturing 2008 and system integration 2010, for example, by substantially expediting assembly of or reducing the cost of an aircraft 2002. Similarly, one or more of apparatus embodiments, method embodiments, or a combination thereof may be utilized while the aircraft 2002 is in service, for example and without limitation during the maintenance and service 2016. For example, the techniques and systems described herein may be used for material procurement 2006, component and subassembly manufacturing 2008, system integration 2010, service 2014, and/or maintenance and service 2016, and/or may be used for airframe 2018 and/or interior 2022. These techniques and systems may even be utilized for systems 2020, including, for example, propulsion system 2024, electrical system 2026, hydraulic 2028, and/or environmental system 2030.

In one embodiment, a part comprises a portion of airframe 2018, and is manufactured during component and subassembly manufacturing 2008. The part may then be assembled into an aircraft in system integration 2010, and then be utilized in service 2014 until wear renders the part unusable. Then, in maintenance and service 2016, the part may be discarded and replaced with a newly manufactured part. Inventive components and methods may be utilized throughout component and subassembly manufacturing 2008 in order to fabricate laminates that are hardened into new parts.

Any of the various control elements (e.g., electrical or electronic components) shown in the figures or described herein may be implemented as hardware, a processor implementing software, a processor implementing firmware, or some combination of these. For example, an element may be implemented as dedicated hardware. Dedicated hardware elements may be referred to as "processors", "controllers", or some similar terminology. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, a network processor, application specific integrated circuit (ASIC) or other circuitry, field programmable gate array (FPGA), read only memory (ROM) for storing software, random access memory (RAM), non-volatile storage, logic, or some other physical hardware component or module.

Also, a control element may be implemented as instructions executable by a processor or a computer to perform the functions of the element. Some examples of instructions are software, program code, and firmware. The instructions are operational when executed by the processor to direct the processor to perform the functions of the element. The instructions may be stored on storage devices that are readable by the processor. Some examples of the storage devices are digital or solid-state memories, magnetic storage media such as a magnetic disks and magnetic tapes, hard drives, or optically readable digital data storage media.

Although specific embodiments are described herein, the scope of the disclosure is not limited to those specific embodiments. The scope of the disclosure is defined by the following claims and any equivalents thereof.

What is claimed is:

1. A method of detecting out of tolerance inconsistencies during a tape laying process, the method comprising:
   heating a surface of a laminate on which a tape will be applied;
   acquiring an IR image of the surface via an IR camera disposed upstream of a compaction roller of a head of a tape layup machine that applies the tape to the surface, while the tape layup machine places the tape, to scan the surface;
   analyzing the IR image by determining sizes of features depicted in the image, to distinguish out of tolerance features from features that are within tolerance; and
   in the circumstance that an out of tolerance feature is depicted in the IR image, determining, during layup of the tape onto the surface, that the out of tolerance feature is depicted in the IR image, based on the size of the out of tolerance feature.

2. The method of claim 1 wherein:
   pixel values within the IR image correspond with temperatures, and the method further comprises:
      identifying regions that have different temperatures, based on differences between values of neighboring pixels; and
      assigning neighboring pixels that have differences in temperature of more than one degree Fahrenheit to different regions.

3. The method of claim 2 further comprising:
   determining whether a region represents a lane of tape or the surface, based on temperatures of the regions.

4. The method of claim 2 wherein:
   neighboring pixels that have differences in temperature between one and fifty degrees Fahrenheit are assigned to different regions.

5. The method of claim 1 further comprising:
   determining a direction of the tape;
   for each lane of the tape, identifying a boundary at which temperature changes by more than a threshold amount when proceeding in the direction; and
   for each lane of the tape, determining a location of a corresponding boundary, comprising:
      determining a position of an infrared camera that performs IR imaging, at a time when a thermographic image was generated;
      determining a coordinate of the boundary as depicted within the thermographic image; and
      determining the location based on the position of the infrared camera and the coordinate of the corresponding boundary.

6. A portion of an aircraft assembled according to the method of claim 1.

7. A method of inspecting a composite surface comprising:
   creating temperature differentials on a surface that has been heated;
   detecting the temperature differentials on the surface via an IR camera disposed upstream of a compaction roller of a head of a tape layup machine that applies tape to the surface, while the tape layup machine places the tape, to scan the surface;
   analyzing the IR image by determining sizes of features depicted in the image, to distinguish out of tolerance features from features that are within tolerance; and
   in the circumstance that an out of tolerance feature is depicted in the IR image, determining, during layup of the tape onto the surface, that the out of tolerance feature is present based upon the temperature differentials and based on sizes of the features.

8. The method of claim 7 wherein:
   detecting the temperature differentials comprises acquiring thermographic images, pixel values within thermographic images correspond with temperatures, and the method further comprises:
      identifying regions that have different temperatures, based on differences between values of neighboring pixels; and
      assigning neighboring pixels that have differences in temperature of more than one degree Fahrenheit to different regions.

9. The method of claim 8 further comprising:
   determining whether a region represents a lane of tape or the surface, based on temperatures of the regions.

10. The method of claim 8 wherein:
    neighboring pixels that have differences in temperature between one and fifty degrees Fahrenheit are assigned to different regions.

11. The method of claim 7 further comprising:
    determining a direction of the tape;
    for each lane of the tape, identifying a boundary at which temperature changes by more than a threshold amount when proceeding in the direction; and
    for each lane of the tape, determining a location of a corresponding boundary at the laminate, comprising:
       determining a position of an infrared camera that performs IR imaging, at a time when a thermographic image was generated;
       determining a coordinate of the boundary as depicted within the thermographic image; and
       determining the location based on the position of the infrared camera and the coordinate of the corresponding boundary.

12. A portion of an aircraft assembled according to the method of claim 7.

13. A method of creating a composite structure comprising:

inspecting a surface on which a laminate is to be laid, with IR imaging, via an IR camera disposed upstream of a compaction roller of a head of a tape layup machine;

reviewing the IR imaging for out of tolerance conditions, based on sizes of features in the IR imaging; and stopping tape layup prior to reaching an out of tolerance condition.

14. The method of claim 13 further comprising:

detecting temperature differentials by acquiring thermographic images, wherein pixel values within thermographic images correspond with temperatures;

identifying regions that have different temperatures, based on differences between values of neighboring pixels; and assigning neighboring pixels that have differences in temperature of more than one degree Fahrenheit to different regions.

15. The method of claim 14 further comprising:

determining whether a region represents a lane of tape or the surface, based on temperatures of the regions.

16. The method of claim 13 further comprising:

determining a direction of the tape;

for each lane of the tape, identifying a boundary at which temperature changes by more than a threshold amount when proceeding in the direction; and for each lane of the tape, determining a location of a corresponding boundary at the laminate, comprising:
  determining a position of an infrared camera that performs IR imaging, at a time when a thermographic image was generated;
  determining a coordinate of the boundary as depicted within the thermographic image; and
  determining the location based on the position of the infrared camera and the coordinate of the corresponding boundary.

17. A portion of an aircraft assembled according to the method of claim 13.

18. A method comprising:

laying up lanes of tape at a laminate;

operating an IR camera disposed upstream of a compaction roller of a head of a tape layup machine to thermally image the lanes of tape;

reviewing thermal images to identify ends of the lanes of tape, based on sizes of features in the thermal images; and determining whether an end of a lane of tape is out of tolerance; and in the circumstance that the end of the lane of tape is out of tolerance, reporting the out of tolerance end of the lane of tape for dispositioning.

19. The method of claim 18 further comprising:

detecting temperature differentials by acquiring thermographic images, wherein pixel values within thermographic images correspond with temperatures;

identifying regions that have different temperatures, based on differences between values of neighboring pixels; and assigning neighboring pixels that have differences in temperature of more than one degree Fahrenheit to different regions.

20. The method of claim 19 further comprising:

determining whether a region represents a lane of tape or the surface, based on temperatures of the regions.

21. The method of claim 18 further comprising:

determining a direction of the tape;

for each lane of the tape, identifying a boundary at which temperature changes by more than a threshold amount when proceeding in the direction; and for each lane of the tape, determining a location of a corresponding boundary at the laminate, comprising:
  determining a position of an infrared camera that performs IR imaging, at a time when a thermographic image was generated;
  determining a coordinate of the boundary as depicted within the thermographic image; and
  determining the location based on the position of the infrared camera and the coordinate of the corresponding boundary.

22. A portion of an aircraft assembled according to the method of claim 18.

* * * * *